US012622239B2

(12) United States Patent
Glavin et al.

(10) Patent No.: US 12,622,239 B2
(45) Date of Patent: May 5, 2026

(54) SENSOR COMPRISING PATTERN ILLUMINATION-BASED ANNEALED COATED SUBSTRATE AND ONE OR MORE FUNCTIONAL MOLECULES AND PROCESS OF USING SAME

(71) Applicant: Government of the United States, as represented by the Secretary of the Air Force, Wright-Patterson AFB, OH (US)

(72) Inventors: Nicholas R. Glavin, Springboro, OH (US); Christopher Muratore, Kettering, OH (US); Melani K. Muratore, Kettering, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 1158 days.

(21) Appl. No.: 17/336,799

(22) Filed: Jun. 2, 2021

(65) Prior Publication Data

US 2021/0313188 A1 Oct. 7, 2021

Related U.S. Application Data

(63) Continuation-in-part of application No. 17/216,729, filed on Mar. 30, 2021.

(Continued)

(51) Int. Cl.
*H01L 21/324* (2006.01)
*G01N 33/52* (2006.01)
(Continued)

(52) U.S. Cl.
CPC ............ *H10P 95/90* (2026.01); *G01N 33/52* (2013.01); *H10D 62/80* (2025.01); *H10P 74/207* (2026.01)

(58) Field of Classification Search
CPC ................ H01L 21/324; H01L 21/428; H10L 21/02675
See application file for complete search history.

(56) References Cited

U.S. PATENT DOCUMENTS 3,138,743 A 6/1964 Kilby
5,515,241 A 5/1996 Werther
(Continued)

OTHER PUBLICATIONS

Kukkar et al. "A New Electrolytic Synthesis Method for Few Layered MoS2 Nanosheets and Their Robust Biointerfacing With Reduced Antibodies." ACS Applied Materials & Interfaces, 8, 16555-16563 (2016). DOI: 10.1021/acsami.6b03079. (Year: 2016).*
(Continued)

*Primary Examiner* — Yara B Green
*Assistant Examiner* — Erika H Son
(74) *Attorney, Agent, or Firm* — AFMCLO/JAZ; Jeffrey V. Bamber; James F. McBride

(57) ABSTRACT

The present invention relates to sensors comprising pattern illumination-based annealed coated substrate and one or more functional molecules and process of using same. Such process yields components that can have one or more electronic and/or optical functionalities that are integrated on the same substrate or film and to which one or more functional molecules can be attached to yield a sensor. In addition, such process does not require large-scale clean rooms and is easily configurable. Thus, rapid device prototyping, design change and evolution in the lab and on the production side is realized. The resulting sensors provide a (Continued)

sensing capability that is as good as or better than current sensors and can be tailored to sense specific biomaterials and/or chemicals.

27 Claims, 15 Drawing Sheets

Specification includes a Sequence Listing.

Related U.S. Application Data

(60) Provisional application No. 63/001,604, filed on Mar. 30, 2020.

(51) Int. Cl.

| | |
|---|---|
| *H01L 21/66* | (2006.01) |
| *H10D 62/80* | (2025.01) |
| *H10P 74/20* | (2026.01) |
| *H10P 95/90* | (2026.01) |

(56) References Cited

U.S. PATENT DOCUMENTS

| | | | | |
|---|---|---|---|---|
| 5,526,280 | A | 6/1996 | Consadori et al. | |
| 10,429,381 | B2 | 10/2019 | Hoffman | |
| 10,770,483 | B2 * | 9/2020 | Sugawara | H10D 30/6756 |
| 10,875,339 | B1 | 12/2020 | Claussen | |
| 11,469,351 | B2 * | 10/2022 | Li | H10F 77/12 |
| 12,123,845 | B2 * | 10/2024 | Mahjouri-Samani | |
| | | | | G01N 27/4145 |
| 2006/0246632 | A1 | 11/2006 | Okumura | |
| 2012/0043546 | A1 | 2/2012 | Oh | |
| 2018/0308692 | A1 * | 10/2018 | Muratore | H10D 62/80 |
| 2020/0090933 | A1 | 3/2020 | Muratore | |
| 2021/0299781 | A1 | 9/2021 | Glavin et al. | |
| 2021/0299789 | A1 | 9/2021 | Glavin et al. | |
| 2021/0301381 | A1 | 9/2021 | Glavin et al. | |
| 2021/0325380 | A1 | 10/2021 | Muthukumar | |
| 2022/0140147 | A1 * | 5/2022 | Choe | H10D 1/68 |
| | | | | 257/295 |
| 2022/0270891 | A1 * | 8/2022 | Currie | H01L 21/477 |
| 2023/0045818 | A1 | 2/2023 | Glavin et al. | |
| 2023/0148461 | A9 | 5/2023 | Glavin et al. | |
| 2023/0152309 | A9 | 5/2023 | Glavin et al. | |

OTHER PUBLICATIONS

Castellanos-Gomez et al. "Laser-thinning of MoS2: On-Demand Generation of a Single-Layer Semiconductor." Nano Letters. vol. 12, No. 6, 3187-3192 (2012). DOI: 10.1021/nl301164v. (Year: 2012).*

Li et al. ("Fibroin-like Peptides Self-Assembling on Two-Dimensional Materials as a Molecular Scaffold for Potential Biosensing." ACS Applied Materials & Interfaces, 11, 20670-20677 (2019). DOI: 10.1021/acsami.9b04079). (Year: 2019).*

Zhang et al. ("DNA-based functionalization of two-dimensional MoS2 FET biosensor for ultrasensitive detection of PSA." Applied Surface Science, 548, 149169 (2021). DOI: 10.1016/j.apsusc.2021. 149169). (Year: 2021).*

Wang et al. ("Functionalized MoS2 Nanosheet-Based Field-Effect Biosensor for Label-Free Sensitive Detection of Cancer Marker Proteins in Solution." Small (Weinheim an der Bergstrasse, Germany), 10(6), 1101-1105 (2014). DOI: 10.1002/smll.201302081). (Year: 2014).*

Austin Drake et al: "Laser writing of electronic circuitry in thin film molybdenum disulfide: A transformative manufacturing approach", Materials Today 2020, 43, pp. 17-26.

Yi Rang Lim et al: "Roll-to-Roll Production of Layer-Controlled Molybdenum Disulfide: A Platform for 2D Semiconductor-Based Industrial Applications", Advanced Materials, 2018, 30,1705270, pp. 1-8.

Rai Rachel H et al: "Pulsed laser annealing of amorphous two-dimensional transition metal dichalcogenides" J. Vac. Sci. Technol. 2020, A 38, 052201, pp. 1-7.

PCT International Search Report for PCT/US22/20854.

PCT Written Opinion of The International Searching Authority for PCT/US22/20854.

U.S. Appl. No. 17/216,729 Nov. 25, 2024 Non-final Rejection.

Mine, H.; Kobayashi, A.; Nakamura, T.; Inoue, T.; Pakdel, S.; Marian, D.; Gonzalez-Marin, E.; Maruyama, S.; Katsumoto, S.; Fortunelli, A.; Palacios, J.J.; Haruyama, J .; Laser-Beam-Patterned Topological Insulating States on Thin Semiconducting MoS2 2019, Physical Review Letters 123, 146803.

Tan, Y.; Luo, F.; Zhu, M.; Xu, X.; Ye, Y.; Li, B.; Wang, G.; Luo, W.; Zheng, X.; Wu, N.; Yu, Y.; Qin, S.; Zhang, X.; Controllable 2H-to-1T' phase transition in few-layer MoTe2 Nanoscale 2018, 10, 19964-19971.

PCT International Search Report for PCT/US22/20850.

PCT Written Opinion of the International Searching Authority for PCT/US22/20850.

PCT International Search Report for PCT/US22/20851.

PCT Written Opinion of the International Searching Authority for PCT/US22/20851.

PCT International Search Report for PCT/US22/20853.

PCT Written Opinion of the International Searching Authority for PCT/US22/20853.

McConny, M.E. et al.; "Direct synthesis of ultra-thin large area transition metal dichalcogenides and their heterostructures on stretchable polymer surfaces," J. of Mat. Res., 2016, 0, 0, 1-8.

Sirota, B. et al. "Room temperature magnetron sputtering and laser annealing of ultrathin MoS2 for flexible transistors," Vacuum, 2019, 160, 133-138.

Kim, R. H. et al.; "Photonic Crystallization of MoS2 for Stretchable Photodetectors," Nanoscale, 2019, 11, 13260-13268.

Galvin, N. R.; IEEE Presentation Rapid Conference in Miramar Beach, FL. Aug. 20, 2019, 1-44.

Ahmadi, Z. et al "Self-limiting laser crystallization and direct writing of 2D materials" Int. J. Extrem. Manuf. 2019, 1, 015001, 1-8.

Vilá, R. A. . et al "In situ crystallization kinetics of two-dimensional MoS2" 2D Mater. 5 2018, 5, 011009, 1-8.

Muratore, C. "Biofunctionalized Two-dimensional MoS2 Receptors for Rapid Response Modular Electronic SARS-CoV-2 and Influenza A Antigen Sensors" medrxivorg., Nov. 20, 2020, 1-11.

Muratore, C. "Beyond point of care diagnostics: Lowdimensional nanomaterials for electronic virus sensing" J. Vac. Sci. Technol. A 2020, 38, 050804, 1-16.

U.S. Appl. No. 17/216,729 Apr. 21, 2025 Final Rejection.

U.S. Appl. No. 17/336,799 Mar. 31, 2025 Non-final Rejection.

U.S. Appl. No. 17/523,705 Jun. 5, 2025 Non-final Rejection.

U.S. Appl. No. 17/523,721 Apr. 15, 2025 Non-final Rejection.

U.S. Appl. No. 17/957,293 Apr. 15, 2025 Non-final Rejection.

Supplemental information for Kukkar, et al. "A New Electrolytic Synthesis Method for Few Layered MoS2 Nanosheets and Their Reduced Antibodies", ACS Applied Materials & Interfaces, 8, 16555-16563 (2016). DOI: 10.1021/acsami.6b03079. (Year: 2016).

Zhang, et al. "Protocell arrays for simulatneous detection of diverse analytes", Nat Commun 12, 5724 (2001). DOE: 10.1038/s41467-021-25989-3. (Year: 2021).

Lee, et al. "Two-dimensional Layered MoS2 Biosensors Enable Highly Sensitive Detection of Biomolecules", Sci Rep 4, 7352 (2014). DOI: 10.1038/srep07352. (Year: 2014).

Windom, et al. "A Raman Spectroscopic Study of MoS2 and MoO3: Applications to Tribological Systems", Tribol Lett 42, 301-310 (2011). DOI: 10.1007/s11249-011-9774-x) (Year: 2011).

Lu, et al., "Layer-by-layer thinning of MoS2 by thermal annealing", Nanoscale 5, 8904-8908 (2013). DOI: 10.1039/c3nr03101b (Year: 2013).

Li, et al., "The Stability of Metallic MoS2 Nanosheets and Their Property Change by Annealing", Nanomaterials, 9, 1366 (2019). DOI: 10.3390/nano9101366. (Year: 2019).

Kang, et al., "High-performance MoS2 transistors with low-resistance molybdenum contacts", Applied Physics Letters 104, 093106 (2014). DOI: 10.1063/1.4866340. (Year: 2014).

(56)     References Cited

OTHER PUBLICATIONS

U.S. Appl. No. 17/336,855 Feb. 13, 2025 Non-final Rejection.

U.S. Appl. No. 17/336,855, filed Sep. 12, 2025 Non-final Rejection.

U.S. Appl. No. 17/523,705, filed Oct. 31, 2025 Final Rejection.

U.S. Appl. No. 17/957,293, filed Nov. 28, 2025 Final Rejection.

Naylor et al. ("Scalable Production of Molybdenum Disulfide Based Biosensors." ACS Nano, 10(6), 6173-6179 (2016). DOI: 10.1021 /acsnano.6b02137). (Year: 2016).

Rajeev et al. ("Laser patterned polymer/nanotube composite electrodes for nanowire transistors on flexible substrates." arXiv: Applied Physics (2017). DOI: 10.48550/arXiv.1711.06925). (Year: 2017).

Kang et al. ("Controllable atomic-ratio of CVD-grown MoS2—MoO2 hybrid catalyst by soft annealing for enhancing hydrogen evolution reaction." International Journal of Hydrogen Energy, 45, 1399-1408 (2020). DOI: 10.1016/j.ijhydene.2019.11.066). (Year: 2019).

Wells et al. ("Roll-to-Roll Deposition of Semiconducting 20 Nanoflake Films of Transition Metal Dichalcogenides for Optoelectronic Applications." ACS Appl. Nano Mater., 2, 7705-7712 (2019). DOI: 10.1021/acsanm.9b01774). (Year: 2019).

Park et al. ("Laser-directed synthesis of strain-induced crumpled MoS2 structure for enhanced triboelectrification toward haptic sensors." Nano Energy, 78, 105266 (2020). DOI: 10.1016/j.nanoen. 2020.105266). (Year: 2020).

* cited by examiner

SENSOR COMPRISING PATTERN ILLUMINATION-BASED ANNEALED COATED SUBSTRATE AND ONE OR MORE FUNCTIONAL MOLECULES AND PROCESS OF USING SAME

CROSS-REFERENCE TO RELATED APPLICATION

The present application is a continuation-in-part of U.S. patent application Ser. No. 17/216,729 filed Mar. 30, 2021, which in turn claims priority to U.S. Provisional Application Ser. No. 63/001,604 filed Mar. 30, 2020, the contents of U.S. patent application Ser. No. 17/216,729 and U.S. Provisional Application Ser. No. 63/001,604 hereby incorporated by reference in its entry.

RIGHTS OF THE GOVERNMENT

The invention described herein may be manufactured and used by or for the Government of the United States for all governmental purposes without the payment of any royalty.

FIELD OF THE INVENTION

The present invention relates to sensors comprising pattern illumination-based annealed coated substrate and one or more functional molecules and process of using same.

BACKGROUND OF THE INVENTION

Current sensors that are used to sense/detect materials such as viruses, bacteria and chemicals are costly to make and/or use. Thus, the use of such sensors are more limited than desired. What is needed is a sensor that can be made quickly, in large numbers—even in millions per day—and yet still provide a sensor capability that is as good as or better than current sensors. Furthermore, unlike current sensors, it is desirable that any new sensor be more accurate and more specific with respect to the material that is detected.

Applicants recognized that the source of the problems associated with current sensors were the processing challenges associated with achieving the required size of the active region of the sensor, sensor chemical and structural uniformity from sensor to sensor that were driven by the complexity of the chemical and physical steps of current production processes. Such recognition led Applicants to develop a process of making the substrate components for sensors that can readily transformed into sensors by attaching a biomaterial there to. Such process employs localization of such material transformations, thereby allowing added flexibility in performing steps for sensor processing, such as application and patterning of electrical contacts prior to application of active electronic material. Importantly, Applicants process can be used to make structural and/or chemical changes within a film or other article that results in an electrical component, an optical component or a combined electrical and optical component being created in such film or article to which a biomaterial is attached to yield a sensor. Such process does not require large-scale clean rooms and is easily configurable. Thus, rapid device prototyping, design change and evolution in the lab and on the production side are realized.

SUMMARY OF THE INVENTION

The present invention relates to sensors comprising pattern illumination-based annealed coated substrate and one or more functional molecules and process of using same. Such process yields components that can have one or more electronic and/or optical functionalities that are integrated on the same substrate or film and to which one or more functional molecules can be attached to yield a sensor. In addition, such process does not require large-scale clean rooms and is easily configurable. Thus, rapid device prototyping, design change and evolution in the lab and on the production side is realized. The resulting sensors provide a sensing capability that is as good or better than current sensors and can be tailored to sense specific biomaterials and/or chemicals Additional objects, advantages, and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Definitions

Figure 1:
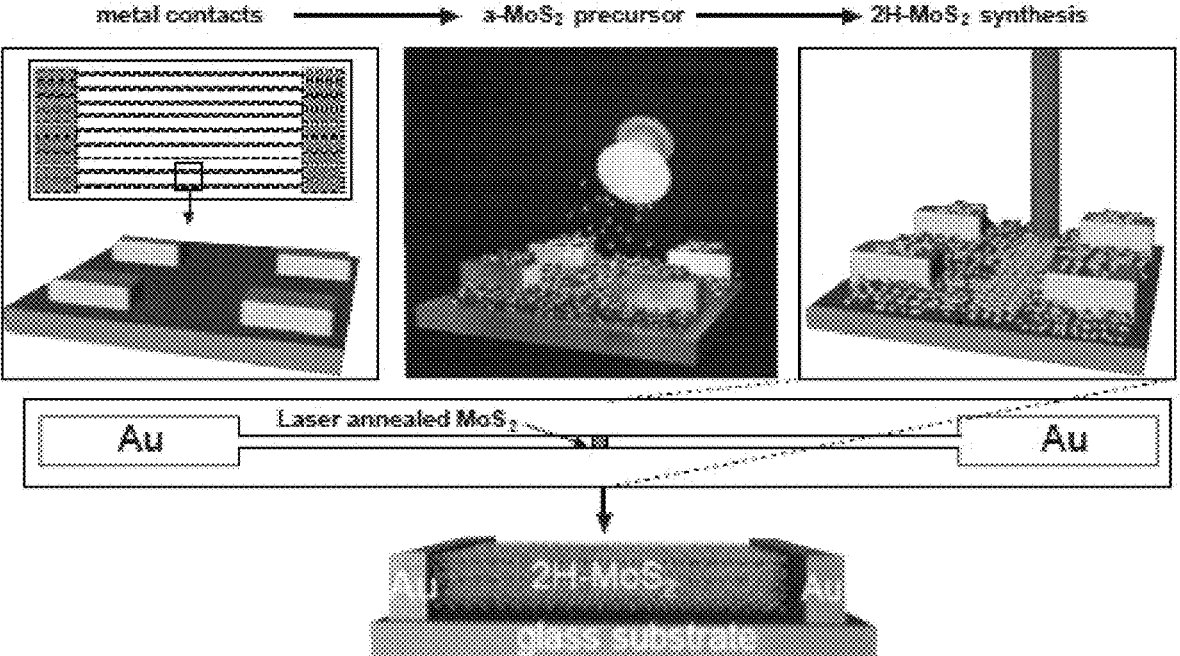
FIG. 1 is a schematic depicting the process of coating $MoS_2$ onto patterned metal contacts followed by laser conversion to 2H-phase $MoS_2$ device.

Unless specifically stated otherwise, as used herein, the terms "a", "an" and "the" mean "at least one".

As used herein, the terms "include", "includes" and "including" are meant to be non-limiting.

As used herein, the words "about," "approximately," or the like, when accompanying a numerical value, are to be construed as indicating a deviation as would be appreciated by one of ordinary skill in the art to operate satisfactorily for an intended purpose.

As used herein, the words "and/or" means, when referring to embodiments (for example an embodiment having elements A and/or B) that the embodiment may have element A alone, element B alone, or elements A and B taken together.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Process of Making Sensor Comprising Pattern Illumination-Based Annealed Coated Substrate and One or More Functional Molecules For purposes of this specification, headings are not considered paragraphs and thus this paragraph is paragraph thirty-three of the present specification. The individual number of each paragraph above and below this paragraph can be determined by reference to this paragraph's number. In this paragraph thirty-three, Applicants disclose a process of making a sensor, said process comprising;

a.) pattern illumination-based annealing a coated substrate comprising a substrate having a first side and a second side, (i) said substrate's first side comprising; one or more coatings of patterned electrical conductive material disposed over said substrate's first side, preferably said patterned electrical conductive material comprises a material selected from the group consisting of poly(3,4-ethylenedioxythiophene), poly(3,4-ethylenedioxythiophene) polystyrene sulfonate, poly(pyrrole), polycarbazoles, polyindoles, polyazepines, Cr, Mo, Ti, Sc, Ni, V, Hf, W, Nb, Au, Ag, Cu, and Pt and mixtures thereof, more preferably said patterned electrical conductive material comprises a metal selected from the group consisting of Cr, Mo, Ti, Sc, Ni, V, Hf, W, Nb, Au, Ag, Cu, and Pt and mixtures thereof, most preferably said metal comprises a metal selected from the group consisting of Mo, Cr, Ti, Au and mixtures thereof, most preferably said one or more coatings of patterned electrical conductive material is a coating of Mo, a coating of Cr and a second coating of Au over said coating of Cr or a coating of Ti and a second coating of Au over said coating of Ti; and one or more chemical coatings disposed over said one or more coatings of patterned electrical conductive material, said one or more chemical coatings each independently comprising a transition metal and an element selected from the group consisting of hydrogen, carbon, nitrogen, oxygen, sulfur, selenium, phosphorous and mixtures thereof, preferably said one or more chemical coatings each independently comprises a transition metal and an element selected from the group consisting of oxygen, sulfur, selenium and mixtures thereof, said one or more chemical coatings each independently comprising at least one of an amorphous, nanocrystalline, microcrystalline or crystalline region, preferably said chemical coatings comprises one or more transition metal dichalcogenides, preferably said one or more transition metal dichalcogenides are selected from the group consisting of $MoS_2$, $WS_2$, $MoSe_2$, $WSe_2$, and mixtures thereof, (ii) said substrate's second side optionally comprising one or more coatings of patterned electrical conductive material disposed over said substrate's first side, preferably said patterned electrical conductive material comprises a material selected from the group consisting of poly(3,4-ethylenedioxythiophene), poly(3,4-ethylenedioxythiophene) polystyrene sulfonate, poly(pyrrole), polycarbazoles, polyindoles, polyazepines, Cr, Mo, Ti, Sc, Ni, V, Hf, W, Nb, Au, Ag, Cu, and Pt and mixtures thereof, more preferably said patterned electrical conductive material comprises a metal selected from the group consisting of Cr, Mo, Ti, Sc, Ni, V, Hf, W, Nb, Au, Ag, Cu, and Pt and mixtures thereof, most preferably said metal comprises a metal selected from the group consisting of Mo, Cr, Ti, Au and mixtures thereof, most preferably said one or more coatings of patterned electrical conductive material is a coating of Mo, a coating of Cr and a second coating of Au over said coating of Cr or a coating of Ti and a second coating of Au over said coating of Ti; and one or more chemical coatings disposed over said one or more coatings of patterned electrical conductive material, said one or more chemical coatings each independently comprising a transition metal and an element selected from the group consisting of hydrogen, carbon, nitrogen, oxygen, sulfur, selenium, phosphorous and mixtures thereof, preferably said one or more chemical coatings each independently comprises a transition metal and an element selected from the group consisting of oxygen, sulfur, selenium and mixtures thereof, said one or more chemical coatings each independently comprising at least one of an amorphous, nanocrystalline, microcrystalline or crystalline region, preferably said chemical coatings comprises one or more transition metal dichalcogenides, preferably said one or more transition metal dichalcogenides are selected from the group consisting of $MoS_2$, $WS_2$, $MoSe_2$, $WSe_2$ and mixtures thereof, said pattern illumination-based annealing comprising using one or more lasers and/or lamps to achieve at least one of a chemical change or structural change in at least a portion of at least one of said one or more chemical coatings on at least one side of said substrate, and optionally the removal of at least a portion of said chemical coating on at least one side of said substrate;

b.) attaching one or more types of functional molecules and/or one or more complexes comprising one or more types of functional molecules and one or more target molecules (as used herein target molecules can be simple molecules or macromolecules including but not limited to proteins, lipids, and carbohydrates, target molecules include aromatics, aromatic halogens, halocarbon, polar aprotics, volatile organic compounds, hazardous gases, for example, arsenic, radon, nitrogen dioxide, carbon monoxide, carbon dioxide, carbon disulfide, ammonia, napthalene, isoprene, terpenes, methanol, benzyl chloride, hexachloro-1,3-butadiene, tribomomethane, 1,4-dioxane) to at least a portion of said pattern illumination-based anneal coated substrate, said one or types of biomaterial being attached to:

(i) a pattern illumination-based annealed portion of said pattern illumination-based anneal coated substrate;

(ii) a portion of said pattern illumination-based anneal coated substrate that is not pattern illumination-based annealed; or (iii) a portion of said pattern illumination-based anneal coated substrate that is not pattern illumination-based annealed and a portion of said pattern illumination-based anneal coated substrate that is pattern illumination-based annealed;

preferably said one or more types of functional molecules are attached to a pattern illumination-based annealed portion of said pattern illumination-based anneal coated substrate.

Each of said chemical coatings may be disposed over said one or more coatings of patterned electrical conductive material via chemical or physical vapor deposition processes including but not limited to thermal decomposition of one or more precursor gases, thermal evaporation, electron beam evaporation, pulsed laser deposition, magnetron sputtering, pulsed direct current magnetron sputtering, high power impulse magnetron sputtering, and/or molecular beam epitaxy.

Applicants disclose a process of making a sensor according to paragraph thirty-three wherein said one or more functional molecules are biomaterials is selected from the group consisting of peptides, nanozymes, proteins, lipids, carbohydrates and lectins, nucleic acids and mixtures thereof; preferably said biomaterial is selected from the group consisting of peptides, proteins, nucleic acids and mixtures thereof; preferably a) said peptides are selected from the group consisting of assemblies of the 20 most common amino acids interacting with both target analytes and the sensor surface, and mixtures thereof. Such interactions may occur via one or a combination of the mechanisms of hydrogen bonding, Van der Waals forces, and ionic interactions between charged species. Peptides may interact with or bind to the sensor surface without modification, such as the 12-mer peptide having SEQ. ID 1 discovered via peptide panning on the $MoS_2$ surface. Alternatively, amino acids or other molecules may be added to the peptide to promote binding to sensor surfaces or target molecules for detection, such as the peptide having SEQ. 2 demonstrating enhanced interactions that may include binding to laser-processed $MoS_2$ surfaces when terminated with two Leucine amino acids. Expected trends dictating interaction strength and even binding of amino acids in peptides to surfaces, such as hydrophobicity, charge and surface contact, are not always observed in practice due to changes in conformation when bound and other factors. Peptides interacting with the sensor surface may reduce the strength and frequency of nonspecific interactions with samples containing multiple components and may also chemically stabilize the sensor surface. Peptides complementing receptor binding sites for elements of cell-surfaces, transmembrane proteins, antibodies, and enzymes provide a means of rapid, inexpensive, and stable functionalization. For example, the peptide having SEQ. 2 is known to bind to cardiac troponin (cTnI), which is regarded as a biomarker for heart tissue damage. When the peptide is functionalized with two leucine amino acids, binds to both the laser-processed $MoS_2$ sensor surface and cTnI. Peptide binding to targets of interest may include families of peptides bearing a resemblance to binding regions of monoclonal antibodies. For medical diagnostics, another peptide having SEQ. ID 3, is known to bind to alanine aminotransferase, regarded as a biomarker for liver damage. Additional examples of peptides interacting with biological targets of interest may include the peptide having SEQ. ID 4 detecting HIV1 protease, the peptide having SEQ ID 5 detecting trypsin, the peptide having SEQ. ID 6 for detection of Caspase 3, and the peptide having SEQ. ID 7 for detection of MMP-7.

b.) said nanozymes are selected from the group consisting of nanomaterials with intrinsic enzyme-like characteristics, mimicking the catalytic activity of peroxidase, oxidase, catalase, haloperoxidase, glutathione peroxidase, uricase, methane monooxygenase, hydrolase, and superoxide dismutase generally in the form of compound nanoparticles, including $Fe_3O_2$, $Mn_3O_4$, $C_{18}Fe_7N_{18}$, and mixtures thereof;

c.) said proteins are selected from the group consisting of antibodies, antibody fragments, antibody mimics, single domain antibodies, and enzymes and mixtures thereof; amino acids or other molecules may be added or subtracted from these proteins to promote interactions including binding to sensor surfaces. Amino acids or other molecules may also be attached or removed from these proteins to promote interactions between the proteins and the sensor surface such as binding, or molecules may be attached to sensor surface to promote interactions including binding. Fundamental constituents of the 5 types of antibodies may be digested into fragments to produce fragments interacting with sensor surfaces allowing maintenance of the binding region conformation for the desired effect of reducing non-specific interactions with a sample. Additionally, smaller proteins with characteristics allowing specific binding to target biomolecules, analogous to whole antibodies or antibody fragments, may be modified to interact with sensor surfaces or the sensor surfaces may modified to interact with antibodies. Proteins such as antibodies or antibody fragments interacting with the sensor surface may reduce the strength and frequency of nonspecific interactions with samples containing multiple components and may also chemically stabilize the sensor surface. Such interactions may occur via one or a combination of the mechanisms of covalent bonding, hydrogen bonding, Van der Waals forces, and ionic interactions between charged species. This approach of functionalizing sensor surfaces with antibodies or antibody fragments is suitable for antibodies that bind to surface proteins on viruses (such as SARS-CoV2, and Influenza A), bacteria (such as *Streptococcus pyogenes*), and other substances such as hormones (such as human chorionic gonadotropic hormone) and proteins native to the body (e.g., cardiac troponin, cTnI) and substances foreign to the body (such as THC, narcotics). Since antibodies for each of these substances share the same fundamental structural elements for digestion into fragments and use on illumination-crystallized $MoS_2$ sensor surfaces. Enzymes are another biomolecule suitable for promotion of specific interactions. For example, the angiotensin-converting enzyme 2 (ACE2) binds to spike proteins of the SARS-CoV and SARS-CoV-2 virus. Modification of ACE2 enzyme for strengthening interactions between the enzyme and the $MoS_2$ sensor surface could involve attachment of amino acids and/or other molecules to allow binding to both sensor and target analyte. Modification could also involve removal of amino acids and molecules until a region suitable for binding to the target analyte remains.

For electronic sensing, smaller binding molecules generally lead to higher sensitivity, indicating an advantage to using smaller molecules.

d.) said lipids are selected from the group consisting of lipid bilayer arrays and liposomes and mixtures thereof including those used for support of membrane proteins for biosensing e.) said carbohydrates and lectins are selected from the group consisting of natural carbohydrates including monosaccharides, oligosaccharides, polysaccharides, or glycoconjugates with proteins and lipids including glycoproteins, glycolipids, or proteoglycans, glycosyl-transferases and glycosidases and mixtures thereof, and f.) said nucleic acids are selected from the group consisting of deoxyribonucleic acid, ribonucleic acid and mixtures thereof to identify genes and genetic mutations in healthy and diseased tissue and other biomolecular targets.

Applicants disclose a process of making a sensor according to paragraphs thirty-three through thirty-four wherein said biomaterial's attachment to said pattern illumination-based anneal coated substrate comprises at least one of a covalent bond, electrostatic bond or a covalent and electrostatic bond. In one aspect, said at least one covalent bond comprises a disulfide bond.

Applicants disclose a process of making a sensor according to paragraphs thirty-three through thirty-five wherein said attaching said biomaterial's to said pattern illumination-based anneal coated substrate comprises contacting said at least a portion of said pattern illumination-based anneal coated substrate and said one or more types of biomaterials, preferably said contacting said at least a portion of said pattern illumination-based anneal coated substrate with said one or more types of biomaterials comprises contacting said at least a portion of said pattern illumination-based anneal coated substrate with a solution comprising said one or more types of biomaterials, more preferably said contacting said at least a portion of said pattern illumination-based anneal coated substrate with said one or more types of biomaterials comprises contacting at least a portion of said pattern illumination-based anneal coated substrate with a solution comprising said one or more types of biomaterials via at least one of pipetting (manually or with an automated system), spraying, printing, dipping, or any other means of applying a solution to a surface. The biomaterial may be suspended in water or any suitable buffer such as phosphate buffered saline with a concentration of from about 0.0001× PBS to about 100× PBS, preferably from about 0.001× PBS—to about 20× PBS, most preferably from about 0.01× PBS to about 10× PBS, where 1× PBS is a composition of about 137 mM NaCl, 2.7 mM KCl, 10 mM $Na_2HPO_4$, and 1.8 mM $KH_2PO_4$, said water or suitable buffer may have, but is not limited to, a pH from about 6.8 to about 7.4. In order to achieve the desired concentration of one or more types of functional molecules per unit of square area on the active sensor region, a solution comprising from about 0.01 pg/mL to about 100 mg/mL of said one or more types of functional molecules may be applied to the active sensor region, preferably in order to achieve the desired concentration of one or more types of functional molecules per unit of square area on the active sensor region, a solution comprising from about 0.1 pg/mL to about 10 mg/mL of said one or more types of functional molecules may be applied to the active sensor region, more preferably in order to achieve the desired concentration of one or more types of functional molecules per unit of square area on the active sensor region, a solution comprising from about 1,000 pg/mL to about 0.1 mg/mL of said one or more types of functional molecules may be applied to the active sensor region, most preferably in order to achieve the desired concentration of one or more types of functional molecules per unit of square area on the active sensor region, a solution comprising from about 100 pg/mL about 1,000 ng/mL of said one or more types of functional molecules may be applied to the active sensor region.

Applicants disclose a process of making a sensor according to paragraphs thirty-three through thirty-six wherein:

a.) at least one of said one or more chemical coatings comprises two or more regions that are amorphous, nanocrystalline, microcrystalline or crystalline with the proviso that at least two of said regions are not identical with respect to being amorphous, nanocrystalline, microcrystalline or crystalline and said laser or lamp forms on, within or on and within said at least one of said one or more chemical coatings:

(i) at least two electronic elements selected from a conductor, semiconductor and an insulator;

(ii) two or more different conductors having at least one of the following: different electrical properties or different optical properties;

(iii) two or more different semiconductors having at least one of the following: different electrical properties or different optical properties; or (iv) two or more different insulators having at least one of the following: different electrical properties or different optical properties;

said process being performed under one of the following conditions: vacuum of less 100 torr, air or under a fluid blanket other than air;

said pattern illumination-based annealing resulting in at least one of a chemical change or structural change, and the removal of at least a portion of at least one of said one or more chemical coatings and resulting in an electrical component, an optical component or a combined electrical and optical component being formed on, within or on and within at least a portion of said pattern illumination-based annealed one or more chemical coatings; or b) at least one of said one or more chemical coatings comprises at least one region that is amorphous, nanocrystalline, microcrystalline or crystalline, and said one or more lasers and/or lamps forms on, within or on and within said at least one of said one or more chemical coatings:

(i) at least two electronic elements selected from a conductor, semiconductor and an insulator;

(ii) two or more different conductors having at least one of the following: different electrical properties or different optical properties;

(iii) two or more different semiconductors having at least one of the following: different electrical properties or different optical properties; or (iv) two or more different insulators having at least one of the following: different electrical properties or different optical properties;

said process being performed under one of the following environmental conditions: vacuum of less than 100 torr, air or under a fluid blanket other than air, then repeating, one or more times said pattern illumination-based annealing on said portion of said one or more chemical coatings using one or more of the following:

(i) the same device but at least one of the following: a different intensity or time;

(ii) a different environmental condition from the previous environmental condition, said different environmental condition select from the same group of environmental conditions; or (iii) a lamp if the previous pattern illumination-based annealing was laser pattern illumination-based annealing or a laser if the previous pattern illumination-based annealing was lamp pattern illumination-based annealing said pattern illumination-based annealing resulting in at least one of a chemical change or structural change, and the removal of at least a portion of at least one of said one or more chemical coatings and resulting in an electrical component, an optical component or a combined electrical and optical component being formed on, within or on and within at least a portion of said pattern illumination-based annealed one or more chemical coatings.

Applicants disclose a process of making a sensor according to paragraph thirty-seven wherein for element b) said at least one chemical coating comprises two or more regions that are amorphous, nanocrystalline, microcrystalline or crystalline with the proviso that at least two of said regions are not identical with respect being amorphous, nanocrystalline, microcrystalline or crystalline, at least two of said regions being pattern illumination-based annealed via different pattern illumination-based annealing processes.

Applicants disclose a process of making a sensor according to paragraphs thirty-three through thirty-eight wherein said transition metal is selected from the group consisting of molybdenum, tungsten, niobium, tantalum, vanadium, titanium, chromium, iron, rhodium, hafnium, rhenium and mixtures thereof.

Applicants disclose a process of making a sensor according to paragraphs thirty-three through thirty-nine wherein said process is performed under a fluid blanket other than air.

Applicants disclose a process of making a sensor according to paragraphs thirty-three through thirty-nine wherein said fluid blanket comprises:

a) an element selected from the group consisting of krypton, xenon, radon, argon, neon, helium, hydrogen, carbon, nitrogen, oxygen, sulfur, selenium, phosphorous and mixtures thereof, b) based on total fluid volume greater than 0% to about 19% or from 21% to 100% oxygen; and/or c) greater than 0% to about 78% or from 80% to 100% nitrogen.

Applicants disclose a process of making a sensor according to paragraphs thirty-three through forty-one wherein said material comprises at least one region that is amorphous or nanocrystalline.

Applicants disclose a process of making a sensor according to paragraphs thirty-three through forty-two wherein said pattern illumination-based annealing is achieved by using one or more lasers, said one or more lasers each being independently selected from a laser that is a pulsed laser, a continuous laser or a pulsed/continuous laser. A pulsed/continuous laser is a laser that can provide a pulsed laser beam and a continuous laser.

Applicants disclose a process of making a sensor according to paragraphs thirty-three through forty-two wherein said pattern illumination-based annealing is achieved by using a continuous wave laser to subject at least a portion of said chemical coating, for a time of about 0.001 milliseconds to 60 seconds to said continuous laser, preferably for a time of about 0.1 milliseconds to 10 seconds to said continuous laser, more preferably for a time of about 1 millisecond to 1 second to said continuous laser; said continuous laser having power of from about 1 microwatt to about 1 megawatt over the time period said at least a portion of said chemical coating is subjected to said continuous laser, preferably said continuous laser having power of from about 0.1 milliwatt to about 1 kilowatt over the time period said at least a portion of said chemical coating is subjected to said continuous laser, more preferably said continuous laser having power of from about 1 microwatt to about 500 watts over the time period said at least a portion of said chemical coating is subjected to said continuous laser; preferably said portion of said chemical coating has an area of about 100 square nanometers to about 1 square meter, more preferably said portion of said chemical coating has an area of about 1 square micrometer to about 1 $cm^2$, most preferably said portion of said chemical coating has an area of about 100 square micrometers to about 250,000 square micrometers. Said portion of said chemical coating may be of any geometry including but not limited to a rectangular, circular or square.

Applicants disclose a process of making a sensor according to paragraphs thirty-three through forty-two wherein said pattern illumination-based annealing is achieved by using a lamp to subject at least a portion of said chemical coating for a time of about 10 microseconds to about 500,000 microseconds, preferably for a time of about 25 microseconds to about 100,000 microseconds, more preferably for a time of about 50 microseconds to about 1,000 microseconds to said lamp, said lamp having power of from about 0.01 $J/cm^2$ to about 1,000 $J/cm^2$, preferably said lamp having power of from about 0.1 $J/cm^2$ to about 100 $J/cm^2$, more preferably said lamp having power of from about 2 $J/cm^2$ to about 10 $J/cm^2$, preferably said portion of said chemical coating has an area of about 1 square micrometer to about 50 square meters, more preferably said portion has an area of about 1 square micrometers to about 1 square meter, most preferably said portion of said chemical coating has an area of about 10 square micrometers to about 1 $cm^2$. Said portion of said chemical coating may be of any geometry including but not limited to a rectangular, circular or square.

Applicants disclose a process of making a sensor according to paragraphs thirty-three through forty-two wherein said pattern illumination-based annealing is achieved by using a pulsed laser to subject at least a portion of said chemical coating for a time of about 0.1 femtoseconds to 60 seconds to said pulsed laser, preferably for a time of about 0.1 nanoseconds to 1 second to said pulsed laser, more preferably for a time of about 10 nanoseconds to 1 millisecond to said pulsed laser; said pulsed laser having a peak power of from about 0.1 microwatt to about 1000 gigawatts over the time period said at least a portion of said chemical coating is subjected to said pulsed laser, preferably said pulsed laser having a peak power of from about 0.1 milliwatt to about 100 megawatts over the time period said at least a portion of said chemical coating is subjected to said pulsed laser, more preferably said pulsed laser having a peak power of from about 1 watt to about 50 megawatts over the time period said at least a portion of said chemical coating is subjected to said pulsed laser; said pulsed laser having a pulse period of about 0.1 femtoseconds to 1 second, preferably said pulsed laser having a pulse period of about 0.1 nanosecond to 1 microsecond, more preferably said pulsed laser having a pulse period of about 1 nanosecond to 100 nanoseconds; preferably said portion of said chemical coating has an area of about 100 square nanometers to about 1 square meter, more preferably said portion of said chemical coating has an area of about 1 square micrometers to about 1 $cm^2$, most preferably said portion of said chemical coating has an area of about 100 square micrometers to about 500 square micrometers. Said portion of said chemical coating may be of any geometry including but not limited to a rectangular, circular or square.

Applicants disclose a process of making a sensor according to paragraphs thirty-three through forty-six wherein, said each chemical coating independently has a thickness of from about 0.1 nanometers to about 1 centimeter.

Applicants disclose a process of making a sensor according to paragraphs thirty-three through forty-six wherein, said each chemical coating independently has a thickness of from about 0.3 nanometers to about 10 micrometers.

Applicants disclose a process of making a sensor according to paragraphs thirty-three through forty-eight wherein, said electrical and/or optical component is selected from the group consisting of an inductor, a capacitor, a resistor, a diode, a transistor, a trace, a battery, an optical filter, a chemical sensor, a biological sensor and a solar cell.

Applicants disclose a process of making a sensor according to paragraphs thirty-three through forty-nine wherein each of said one or more chemical coatings have an area and a thickness and said removal of said at least a portion of said one or more chemical coating occurs, said removal comprising at least one of:

a.) laser ablation removal of from about 0.1% to about 99.9% of at least one of said one or more chemical coatings' area, preferably said removal comprising laser ablation removal of from about 2% to about 98% of at least one of said chemical coatings' area, more preferably said removal comprising laser ablation removal of from about 10% to about 90% of at least one of said chemical coatings' area; or b.) laser ablation removal of at least 85% of at least one of said chemical coatings' thickness, preferably said removal comprises laser ablation removal of at least 95% of at least one of said chemical coatings' thickness; or laser ablation removal of about 85% to about 99% of at least one of said chemical coatings' thickness.

Applicants disclose a process of making a sensor according to paragraphs thirty-three through fifty said process being a roll process wherein said coated chemically substrate is a rolled coated chemically substrate that is unrolled at least in part, said unrolled chemical coating portion of said coated substrate being at least in part pattern illumination-based annealed, preferably said roll process is a continuous process, more preferably said roll process is a roll to roll process wherein said coated substrate is unrolled at least in part, said unrolled portion being, at least in part, pattern illumination-based annealed and rerolled.

Applicants disclose a process of making a sensor according to paragraphs thirty-three through fifty-one wherein said substrate of said coated substrate is selected from glass, polymer and mixtures thereof, preferably said polymer is selected from the group consisting of polyethylene naphthalate, polyimide, polycarbonate, polyethylene naphthalate and polyethylene terephthalate and mixtures thereof.

Applicants disclose a process of making a sensor according to paragraphs thirty-three through fifty-two wherein at least a portion of said coated substrate's pattern illumination-based annealed chemical coating is further treated by at least one of the following processes:

a.) two or more pattern illumination-based annealings; said two more pattern illumination-based annealings may each be independently conducted in accordance with the process disclosed in paragraphs thirty-three through fifty-two;

b.) plasma treatment comprising exposing said at least a portion of said coated substrate's pattern illumination-based annealed chemical coating to an ionized gas derived from the group consisting of He, Ne, Ar, Kr, Xe, $H_2$, $O_2$, $SF_6$, $CF_4$, $N_2$ and mixtures thereof; preferably said plasma treatment comprises exposing said at least a portion of said coated substrate's pattern illumination-based annealed chemical coating to an ionized gas derived from the group consisting of He, Ar, $H_2$, $O_2$, $SF_6$, $CF_4$ and mixtures thereof, more preferably said plasma treatment comprises exposing said at least a portion of said coated substrate's pattern illumination-based annealed chemical coating to an ionized gas derived from the group consisting of Ar, $H_2$, $SF_6$, $CF_4$ and mixtures thereof, most preferably said plasma treatment comprises exposing said at least a portion of said coated substrate's pattern illumination-based annealed chemical coating to an ionized gas derived from the group consisting of Ar, $H_2$ and mixtures thereof;

(i) said plasma treatment being conducted at a pressure of from about 0.1 mTorr to about 1000 Torr, preferably said plasma treatment being conducted at a pressure of about 0.5 mTorr to about 760 Torr, more preferably said plasma treatment being conducted at a pressure of about 1 mTorr to about 100 Torr, most preferably said plasma treatment being conducted at a pressure of about 1 mTorr to about 10 Torr;

(ii) said at least a portion of said coated substrate's pattern illumination-based annealed chemical coating's plasma treatment temperature being from about 0° C. to about 1,500° C., preferably said at least a portion of said coated substrate's pattern illumination-based annealed chemical coating's plasma treatment temperature being from about 5° C. to about 1,000° C., more preferably said at least a portion of said coated substrate's pattern illumination-based annealed chemical coating's plasma treatment temperature being from about 5° C. to about 900° C., most preferably said at least a portion of said coated substrate's pattern illumination-based annealed chemical coating's plasma treatment temperature being from about 18° C. to about 700° C.; and (iii) said at least a portion of said coated substrate's pattern illumination-based annealed chemical coating exposure time being from about 0.001 seconds to about 10,000,000 seconds, preferably said at least a portion of said coated substrate's pattern illumination-based annealed chemical coating exposure time being from about 0.01 seconds to about 1,000,000 seconds, more preferably said at least a portion of said coated substrate's pattern illumination-based annealed chemical coating exposure time being from about 0.1 seconds to about 100,000 seconds, most preferably said at least a portion of said coated substrate's pattern illumination-based annealed chemical coating exposure time being from about 0.1 seconds to about 10,000 seconds. Different modes of plasma generation may include remote plasmas from sources such as electron cyclotron resonance, inductively coupled plasmas, capacitively coupled plasmas, and electron beam generated plasmas. Inductively coupled and glow discharge plasmas by coupling of power to the substrate may also be used alone or in conjunction with a remote plasma source. Plasma power may be continuous or pulsed from frequencies ranging from 0.01 Hz to 10 GHz. The.

c.) ion beam irradiation comprising exposing said at least a portion of said coated substrate's pattern illumination-based annealed chemical coating to an ion beam, said ion beam comprising an ionized gas derived from the group consisting of He, Ne, Ar, Kr, Xe, $H_2$, $O_2$, $SF_6$, $CF_4$, $N_2$ and mixtures thereof; preferably said ion beam comprises an ionized gas derived from the group consisting of He, Ar, $H_2$, $O_2$, $SF_6$, $CF_4$ and mixtures thereof, more preferably said ion beam comprising an ionized gas derived from the group consisting of Ar, $H_2$, $SF_6$, $CF_4$ and mixtures thereof, most preferably said ion beam comprising an ionized gas derived from the group consisting of Ar, $H_2$ and mixtures thereof, (i) said ion beam having an incident ion energy of from about 50 eV to about 10,000 eV, preferably said ion beam having an incident ion energy of from about 100 eV to about 5,000 eV, more preferably said ion beam having an incident ion energy of from about 100 eV to 2000 eV, most preferably said ion beam having an incident ion energy of from about 100 eV to 1000 eV;

(ii) said ion beam having an incoming ion species incident angle of from about 1° to 90°, relative to the surface being bombarded, preferably said ion beam having an incoming ion species incident angle of from about 3° to about 90°, more preferably said ion beam having an incoming ion species incident angle of from about 4° to about 90°, and most preferably said ion beam having an incoming ion species incident angle of from about 5° to about 90°;

(iii) said ion beam having an incident ion flux of from about 0.1 $nA/mm^2$ to about 900,000,000 $nA/mm^2$, preferably said ion beam having an incident ion flux of from about 0.5 $nA/mm^2$ to about 10,000,000 $nA/mm^2$, more preferably said ion beam having an incident ion flux of from about 0.5 to about 1,000,000 $nA/mm^2$, and most preferably said ion beam having an incident ion flux of from about 0.5 to about 900,000 $nA/mm^2$;

(iv) said at least a portion of said coated substrate's pattern illumination-based annealed chemical coating's ion beam irradiation treatment temperature being from about 0° C. to about 1,500° C., preferably said at least a portion of said coated substrate's pattern illumination-based annealed chemical coating's ion beam irradiation treatment temperature being from about 5° C. to about 1,000° C., more preferably said at least a portion of said coated substrate's pattern illumination-based annealed chemical coating's ion beam irradiation treatment temperature being from about 5° C. to about 900° C., most preferably said at least a portion of said coated substrate's pattern illumination-based annealed chemical coating's ion beam irradiation treatment temperature being from about 18° C. to about 700° C.; and (v) said at least a portion of said coated substrate's pattern illumination-based annealed chemical coating's ion beam irradiation exposure time to said ion beam being from about 0.001 seconds to about 10,000,000 seconds, preferably said at least a portion of said coated substrate's pattern illumination-based annealed chemical coating's ion beam irradiation exposure time to said ion beam being from about 0.01 seconds to about 1,000,000 seconds, more preferably said at least a portion of said coated substrate's pattern illumination-based annealed chemical coating's ion beam irradiation exposure time to said ion beam being from about 0.1 seconds to about 100,000 seconds, most preferably at least a portion of said coated substrate's pattern illumination-based annealed chemical coating's ion beam irradiation exposure time to said ion beam being from about 0.1 seconds to about 10,000 seconds; Sensor surface is a means to generate sulfur vacancies d.) electron beam illumination comprising at least a portion of said coated substrate's pattern illumination-based annealed chemical coating to an electron dose of from about $10^2$ electrons/nm$^2$ to about $10^{25}$ electrons/nm$^2$, preferably from about 10' electrons/nm$^2$ to about $10^{22}$ electrons/nm$^2$, more preferably from about $10^4$ electrons/nm$^2$ to about $10^{20}$ electrons/nm$^2$, most preferably from about 10' electrons/nm$^2$ to about $10^{18}$ electrons/nm$^2$ by exposing said at least a portion of said coated substrate's pattern illumination-based annealed chemical coating to:

(i) to an electron beam having an incident electron energy of from about 0.1 eV to about 100,000,000 eV, preferably said electron beam having an incident electron energy of from about 1 eV to about 10,000,000 eV, more preferably said electron beam having an incident electron energy of from about 1 eV to about 1,000,000 eV, most preferably said electron beam having an incident electron energy of from about 1 eV to about 500,000 eV;

(ii) said at least a portion of said coated substrate's pattern illumination-based annealed chemical coating's electron beam illumination exposure time to said electron beam illumination being from about 0.001 seconds to about 10,000,000 seconds, preferably said at least a portion of said coated substrate's pattern illumination-based annealed chemical coating's electron beam illumination exposure time to said electron beam illumination being from about 0.01 seconds to about 1,000,000 seconds, more preferably said at least a portion of said coated substrate's pattern illumination-based annealed chemical coating's electron beam illumination exposure time to said electron beam illumination being from about 0.1 seconds to about 100,000 seconds, most preferably at least a portion of said coated substrate's pattern illumination-based annealed chemical coating's electron beam illumination exposure time to said electron beam illumination being from about 0.1 seconds to about 10,000 seconds;

(iii) said at least a portion of said coated substrate's pattern illumination-based annealed chemical coating's electron beam illumination treatment temperature being from about 0° C. to about 1,500° C., preferably said at least a portion of said coated substrate's pattern illumination-based annealed chemical coating's electron beam illumination treatment temperature being from about 5° C. to about 1,000° C., more preferably said at least a portion of said coated substrate's pattern illumination-based annealed chemical coating's electron beam illumination treatment temperature being from about 5° C. to about 900° C., most preferably said at least a portion of said coated substrate's pattern illumination-based annealed chemical coating's electron beam illumination treatment temperature being from about 18° C. to about 700° C.; Electron beam illumination is a means of inducing surface changes on said at least a portion of said coated substrate's pattern illumination-based annealed chemical coating. Such changes improve and/or control sites for physical and/or chemical bonding.

e.) thermal annealing said at least a portion of said coated substrate's pattern illumination-based annealed chemical coating, said at least a portion of said coated substrate's pattern illumination-based annealed chemical coating's thermal annealing treatment temperature being from about 0° C. to about 1,500° C., preferably said at least a portion of said coated substrate's pattern illumination-based annealed chemical coating's thermal annealing treatment temperature being from about 5° C. to about 1,000° C., more preferably said at least a portion of said coated substrate's pattern illumination-based annealed chemical coating's thermal annealing treatment temperature being from about 5° C. to about 900° C., preferably said at least a portion of said coated substrate's pattern illumination-based annealed chemical coating's thermal annealing treatment temperature being from about 18° C. to about 700° C.;

f.) chemically etching said at least a portion of said coated substrate's pattern illumination-based annealed chemical coating comprising contacting said at least a portion of said coated substrate's pattern illumination-based annealed chemical coating with an etching composition, preferably said coated substrate's pattern illumination-based annealed chemical coating is treated in accordance with at least one of the process of Paragraph 0049 a) or Paragraph 0049 b) prior to said contact with said etching composition, preferably said etching composition is a solution, gel or paste, more preferably said etching composition is a solution having an etching concentration of from about 0.00003 mol/L to about 30 mol/L, more preferably said etching composition is a solution having an etching concentration of from about 0.0003 mol/L to about 25 mol/L, more preferably said etching composition is a solution having an etching concentration of from about 0.003 mol/L to about 20 mol/L, most preferably said etching composition is a solution having an etching concentration of from about 0.03 mol/L to about 20 mol/L; said contacting occurring for a time of from about 0.001 seconds to about 10,000,000 seconds, preferably said contacting occurring for a time of from about 0.01 seconds to about 1,000,000 seconds, more preferably said contacting occurring for a time of from about 0.1 seconds to about 100,000 seconds, and most preferably said contacting occurring for a time of from about 0.1 seconds to about 10,000 seconds, said etching composition having a temperature over said contacting time of from about 0° C. to about 200° C., preferably said etching composition having a temperature over said contacting time of from about 5-180° C., more preferably said etching composition having a temperature over said contacting time of from about 10° C. to about 150° C., most preferably said etching composition having a temperature over said contacting time of from about 18° C. to about 100° C. While not being bound by theory, Applicants believe that sulfur and/or selenium vacancies in MoS$_2$ are produced via chemical modification by etching MoS$_2$ in a solution such as sodium hypochlorite (NaClO) solution as provided above.

g.) electro-chemically treating said at least a portion of said coated substrate's pattern illumination-based annealed chemical coating by contacting said at least a portion of said coated substrate's pattern illumination-based annealed chemical coating with a chemical composition comprising an electrolyte and subjecting said contacted at least a portion of said coated substrate's pattern illumination-based annealed chemical coating and said chemical composition comprising an electrolyte to an electrical current, preferably at least a portion of said coated substrate's pattern illumination-based annealed chemical coating is subjected to said electrical current for a time of from about 0.01 seconds to about 60,000 seconds, more preferably at least a portion of said coated substrate's pattern illumination-based annealed chemical coating is subjected to said electrical current for a time of from about 0.1 seconds to about 6,000 seconds, more preferably at least a portion of said coated substrate's pattern illumination-based annealed chemical coating is subjected to said electrical current for a time of from about 1 seconds to about 600 seconds, most preferably at least a portion of said coated substrate's pattern illumination-based annealed chemical coating is subjected to said electrical current for a time of from about 10 seconds to about 60 seconds, preferably said at least a portion of said coated substrate's pattern illumination-based annealed chemical coating's temperature is from about 0° C. to about 200° C. during said time, preferably said at least a portion of said coated substrate's pattern illumination-based annealed chemical coating's temperature is from about 5° C. to about 180° C. during said time, more preferably said at least a portion of said coated substrate's pattern illumination-based annealed chemical coating's temperature is from about 10° C. to about 150° C. during said time, most preferably said at least a portion of said coated substrate's pattern illumination-based annealed chemical coating's temperature is from about 18° C. to about 100° C. during said time, preferably said electrolyte's concentration is from about 0.0005M to about 50 M, more preferably said electrolyte's concentration is from about 0.005M to about 25M, more preferably said electrolyte's concentration is from about 0.05M to about 20M, most preferably said electrolyte's concentration is from about 0.5M to about 10 M, preferably said electrical current has a linear sweep voltammetry sweeping speed of from about 0.001 mV s$^{-1}$ to about 500 mV s$^{-1}$, more preferably said electrical current has a linear sweep voltammetry sweeping speed of from about 0.01 mV s$^{-1}$ to about 250 mV s$^{-1}$, more preferably said electrical current has a linear sweep voltammetry sweeping speed of from about 0.1 mV s$^{-1}$ to about 200 mV s$^{-1}$, most preferably said electrical current has a linear sweep voltammetry sweeping speed of from about 1 mV s$^{-1}$ to about 200 mV s$^{-1}$. For example, the desulfurization of multilayer MoS$_2$ samples is achieved by electro-chemical desulfurization conducted in an electrochemical cell with 0.5 M sulfuric acid (H$_2$SO$_4$).

h.) surface physical modification of at least a portion of said coated substrate's pattern illumination-based annealed chemical coating including but not limited to ball milling or polishing.

Applicants disclose a process of making a sensor according to paragraphs thirty-three through fifty-three wherein each target is independently a chemical target or a biological target.

Sensor Comprising Pattern Illumination-Based Annealed Coated Substrate and One or More Functional Molecules and Method of Use For purposes of this specification, headings are not considered paragraphs and thus this paragraph is paragraph fifty-five of the present specification. The individual number of each paragraph above and below this paragraph can be determined by reference to this paragraph's number. In this paragraph fifty-five, Applicants disclose a sensor comprising a pattern illumination-based annealed, coated substrate comprising a substrate having a first side and a second side and one or more types of functional molecules and/or one or more complexes comprising one or more types of functional molecules and one or more target molecules attached to at least a portion of said pattern illumination-based anneal coated substrate, a.) said substrate's first side comprising;
 (i) one or more coatings of patterned electrical conductive material disposed over said substrate's first side, preferably said patterned electrical conductive material comprises a material selected from the group consisting of poly(3,4-ethylenedioxythiophene), poly(3,4-ethylenedioxythiophene) polystyrene sulfonate, poly(pyrrole), polycarbazoles, polyindoles, polyazepines, Cr, Mo, Ti, Sc, Ni, V, Hf, W, Nb, Au, Ag, Cu, and Pt and mixtures thereof, more preferably said patterned electrical conductive material comprises a metal selected from the group consisting of Cr, Mo, Ti, Sc, Ni, V, Hf, W, Nb, Au, Ag, Cu, and Pt and mixtures thereof, most preferably said metal comprises a metal selected from the group consisting of Mo, Cr, Ti, Au and mixtures thereof, most preferably said one or more coatings of patterned electrical conductive material is a coating of Mo, a coating of Cr and a second coating of Au over said coating of Cr or a coating of Ti and a second coating of Au over said coating of Ti; and
 (ii) one or more chemical coatings disposed over said one or more coatings of patterned electrically conductive material, said one or more chemical coatings each independently comprising a transition metal and an element selected from the group consisting of hydrogen, carbon, nitrogen, oxygen, sulfur, selenium, phosphorous and mixtures thereof, preferably said one or more chemical coatings each independently comprises a transition metal and an element selected from the group consisting of oxygen, sulfur, selenium and mixtures thereof, said one or more chemical coatings each independently comprising at least one of an amorphous, nanocrystalline, microcrystalline or crystalline region, preferably said chemical coatings comprises one or more transition metal dichalcogenides, preferably said one or more transition metal dichalcogenides are selected from the group consisting of MoS$_2$, WS$_2$, MoSe$_2$, WSe$_2$, and mixtures thereof, at least a portion of said one or more chemical coatings being a pattern illumination-based annealed chemical coating;

b.) said substrate's second side optionally comprising:
 (i) one or more coatings of patterned electrical conductive material disposed over said substrate's first side, preferably said patterned electrical conductive material comprises a material selected from the group consisting of poly(3,4-ethylenedioxythiophene), poly(3,4-ethylenedioxythiophene) polystyrene sulfonate, poly(pyrrole), polycarbazoles, polyindoles, polyazepines, Cr, Mo, Ti, Sc, Ni, V, Hf, W, Nb, Au, Ag, Cu, and Pt and mixtures thereof, more preferably said patterned electrical conductive material comprises a metal selected from the group consisting of Cr, Mo, Ti, Sc, Ni, V, Hf, W, Nb, Au, Ag, Cu, and Pt and mixtures thereof, most preferably said metal comprises a metal selected from the group consisting of Mo, Cr, Ti, Au and mixtures thereof, most preferably said one or more coatings of patterned electrical conductive material is a coating of Mo, a coating of Cr and a second coating of Au over said coating of Cr or a coating of Ti and a second coating of Au over said coating of Ti; and (ii) one or more chemical coatings disposed over said one or more coatings of patterned electrical conductive material, said one or more chemical coatings each independently comprising a transition metal and an element selected from the group consisting of hydrogen, carbon, nitrogen, oxygen, sulfur, selenium, phosphorous and mixtures thereof, preferably said one or more chemical coatings each independently comprises a transition metal and an element selected from the group consisting of oxygen, sulfur, selenium and mixtures thereof, said one or more chemical coatings each independently comprising at least one of an amorphous, nanocrystalline, microcrystalline or crystalline region, preferably said chemical coatings comprises one or more transition metal dichalcogenides, preferably said one or more transition metal dichalcogenides are selected from the group consisting of $MoS_2$, $WS_2$, $MoSe_2$, $WSe_2$ and mixtures thereof, at least a portion of said optional one or more chemical coatings being a pattern illumination-based annealed chemical coating. As used herein target molecules can be simple molecules or macromolecules including but not limited to proteins, lipids, and carbohydrates, target molecules include aromatics, aromatic halogens, halocarbon, polar aprotics, volatile organic compounds, hazardous gases, for example, arsenic, radon, nitrogen dioxide, carbon monoxide, carbon dioxide, carbon disulfide, ammonia, napthalene, isoprene, terpenes, methanol, benzyl chloride, hexachloro-1,3-butadiene, tribomomethane, 1,4-dioxane.

Applicants disclose a sensor according to paragraph fifty-five comprising at least one of:

a.) at least one chemical coating comprising two or more regions that are amorphous, nanocrystalline, microcrystalline or crystalline with the proviso that at least two of said regions are not identical with respect being amorphous, nanocrystalline, microcrystalline or crystalline, at least two of said regions being pattern illumination-based annealed via different pattern illumination-based annealing processes; or b.) at least one chemical coating comprising at least one region that is amorphous, nanocrystalline, microcrystalline or crystalline said at least one region being pattern illumination-based annealed two or more times. The sensor of Paragraphs 0055 and 0056 could be produced in accordance with the processes of Paragraphs 0033 through 0054.

Applicants disclose a sensor according to paragraphs fifty-five through fifty-six wherein:

a.) said substrate of said coated substrate is selected from glass, polymer and mixtures thereof, preferably said polymer is selected from the group consisting of polyethylene naphthalate, polyimide, polycarbonate, polyethylene naphthalate and mixtures thereof;

b) said one or more coatings of patterned electrical conductive material is a coating of Mo, a coating of Cr and a second coating of Au over said coating of Cr or a coating of Ti and a second coating of Au over said coating of Ti; and c) said one or more chemical coatings comprises a material selected from the group consisting of $MoS_2$, $WS_2$, $MoSe_2$, $WSe_2$ and mixtures thereof.

Applicants disclose a sensor according to paragraphs fifty-five through fifty-seven wherein said one or more functional molecules are biomaterials selected from the group consisting of peptides, nanozymes, proteins, lipids, carbohydrates and lectins, nucleic acids and mixtures thereof; preferably said biomaterial is selected from the group consisting of peptides, proteins, nucleic acids and mixtures thereof; preferably a) said peptides are selected from the group consisting of assemblies of the 20 most common amino acids interacting with both target analytes and the sensor surface, and mixtures thereof. Such interactions may occur via one or a combination of the mechanisms of hydrogen bonding, Van der Waals forces, and ionic interactions between charged species. Peptides may interact with or bind to the sensor surface without modification, such as the 12-mer peptide having SEQ. ID 1 discovered via peptide panning on the $MoS_2$ surface. Alternatively, amino acids or other molecules may be added to the peptide to promote binding to sensor surfaces or target molecules for detection, such as the peptide having SEQ. 2 demonstrating enhanced interactions that may include binding to laser-processed $MoS_2$ surfaces when terminated with two Leucine amino acids. Expected trends dictating interaction strength and even binding of amino acids in peptides to surfaces, such as hydrophobicity, charge and surface contact, are not always observed in practice due to changes in conformation when bound and other factors. Peptides interacting with the sensor surface may reduce the strength and frequency of nonspecific interactions with samples containing multiple components and may also chemically stabilize the sensor surface. Peptides complementing receptor binding sites for elements of cell-surfaces, transmembrane proteins, antibodies, and enzymes provide a means of rapid, inexpensive, and stable functionalization. For example, the peptide having SEQ. 2 is known to bind to cardiac troponin (cTnI), which is regarded as a biomarker for heart tissue damage. When the peptide is functionalized with two leucine amino acids, binds to both the laser-processed $MoS_2$ sensor surface and cTnI. Peptide binding to targets of interest may include families of peptides bearing a resemblance to binding regions of monoclonal antibodies. For medical diagnostics, another peptide having SEQ. ID 3, is known to bind to alanine aminotransferase, regarded as a biomarker for liver damage. Additional examples of peptides interacting with biological targets of interest may include the peptide having SEQ. ID 4 detecting HIV1 protease, the peptide having SEQ ID 5 detecting trypsin, the peptide having SEQ. ID 6 for detection of Caspase 3, and the peptide having SEQ. ID 7 for detection of MMP-7.

b.) said nanozymes are selected from the group consisting of nanomaterials with intrinsic enzyme-like characteristics, mimicking the catalytic activity of peroxidase, oxidase, catalase, haloperoxidase, glutathione peroxidase, uricase, methane monooxygenase, hydrolase, and superoxide dismutasegenerally in the form of compound nanoparticles, including $Fe_3O_2$, $Mn_3O_4$, $C_{18}Fe_7N_{18}$, and mixtures thereof;

c.) said proteins are selected from the group consisting of antibodies, antibody fragments, antibody mimics, single domain antibodies, and enzymes and mixtures thereof; amino acids or other molecules may be added or subtracted from these proteins to promote interactions including binding to sensor surfaces. Amino acids or other molecules may also be attached or removed from these proteins to promote interactions between the proteins and the sensor surface such as binding, or molecules may be attached to sensor surface to promote interactions including binding. Fundamental constituents of the 5 types of antibodies may be digested into fragments to produce fragments interacting with sensor surfaces allowing maintenance of the binding region conformation for the desired effect of reducing non-specific interactions with a sample. Additionally, smaller proteins with characteristics allowing specific binding to target biomolecules, analogous to whole antibodies or antibody fragments, may be modified to interact with sensor surfaces or the sensor surfaces may modified to interact with antibodies. Proteins such as antibodies or antibody fragments interacting with the sensor surface may reduce the strength and frequency of nonspecific interactions with samples containing multiple components and may also chemically stabilize the sensor surface. Such interactions may occur via one or a combination of the mechanisms of covalent bonding, hydrogen bonding, Van der Waals forces, and ionic interactions between charged species. This approach of functionalizing sensor surfaces with antibodies or anti-body fragments is suitable for antibodies that bind to surface proteins on viruses (such as SARS-CoV2, and Influenza A), bacteria (such as *Streptococcus pyogenes*), and other substances such as hormones (such as human chorionic gonadotropic hormone) and proteins native to the body (e.g., cardiac troponin, cTnI) and substances foreign to the body (such as THC, narcotics). Since antibodies for each of these substances share the same fundamental structural elements for digestion into fragments and use on illumination-crystallized $MoS_2$ sensor surfaces. Enzymes are another biomolecule suitable for promotion of specific interactions. For example, the angiotensin-converting enzyme 2 (ACE2) binds to spike proteins of the SARS-CoV and SARS-CoV-2 virus. Modification of ACE2 enzyme for strengthening interactions between the enzyme and the $MoS_2$ sensor surface could involve attachment of amino acids and/or other molecules to allow binding to both sensor and target analyte. Modification could also involve removal of amino acids and molecules until a region suitable for binding to the target analyte remains. For electronic sensing, smaller binding molecules generally lead to higher sensitivity, indicating an advantage to using smaller molecules.

d.) said lipids are selected from the group consisting of lipid bilayer arrays and liposomes and mixtures thereof including those used for support of membrane proteins for biosensing e.) said carbohydrates and lectins are selected from the group consisting of natural carbohydrates including monosaccharides, oligosaccharides, polysaccharides, or glycoconjugates with proteins and lipids including glycoproteins, glycolipids, or proteoglycans, glycosyl-transferases and glycosidases and mixtures thereof, and f) said nucleic acids are selected from the group consisting of deoxyribonucleic acid, ribonucleic acid and mixtures thereof to identify genes and genetic mutations in healthy and diseased tissue and other biomolecular targets.

Applicants disclose a sensor according to paragraphs fifty-five through fifty-eight wherein said one or more functional molecules' attachment to said pattern illumination-based anneal coated substrate comprises at least one of a covalent bond, electrostatic bond or a covalent and electrostatic bond. In one aspect, said at least one covalent bond comprises a disulfide bond.

Applicants disclose a sensor according to paragraphs fifty-five through fifty-nine wherein said one or more functional molecule's concentration on said pattern illumination-based anneal coated substrate is from about 0.001 nanograms per square centimeter to about 1,000 nanograms per square centimeter, preferably said one or more functional molecule's concentration on said pattern illumination-based anneal coated substrate is from about 0.01 nanograms per square centimeter to about 500 nanograms per square centimeter, more preferably said one or more functional molecule's concentration on said pattern illumination-based anneal coated substrate is from about 0.1 nanograms per square centimeter to about 200 nanograms per square centimeter, most preferably said one or more functional molecule's concentration on said pattern illumination-based anneal coated substrate is from about 0.1 nanograms per square centimeter to about 100 nanograms per square centimeter. The preferred concentration of biomaterial may depend on the geometry and desired sensitivity limit of the sensor device. For example, a smaller sensor geometry can be used to reduce the number of interactions with a species in the applied sample over a given time period to be reduced.

Applicants disclose a method of using a sensor according to paragraphs fifty-five through sixty comprising the steps of:

a.) measuring one or more optical and/or electrical properties of a sensor according to paragraphs fifty-five through sixty after said sensor comprises one or more complexes comprising one or more types of functional molecules and one or more target molecules b.) comparing said one or more optical and/or electrical properties of said sensor to a baseline of said sensor measured before said sensor comprises one or more complexes comprising one or more types of functional molecules and one or more target molecules. The response of the sensor to a biological sample may be measured electrically or optically, or both electrically and optically. Sensor responses indicating presence of a target species may include changes in electrical resistance in a chemresistor configuration, changes in current flow for a transistor configuration, changes in refractive index, changes in photoluminescence intensity or frequency, and other electrical, optical, or combined electrical and optical responses. After testing, the sample can be neutralized, disposed of, recycled, regenerated, and/or reused. The complexes comprising said one or more types of functional molecules and one or more target molecules can from in a time from about 0.001 seconds to about 5,000,000 seconds, preferably the complexes comprising said one or more types of functional molecules and one or more target molecules can from in a time from about 0.1 seconds to about 5,000 seconds; and more preferably the complexes comprising said one or more types of functional molecules and one or more target molecules can from in a time from about 0.1 seconds to about 1,000 seconds.

Suitable amorphous, nanocrystalline, microcrystalline and/or crystalline materials comprising a transition metal and hydrogen, carbon, nitrogen, oxygen, sulfur, selenium, tellurium, and/or phosphorous can be obtained from Plasmaterials (2268 Research Drive, Livermore, CA 94550 USA) and Kurt Lesker (1925 Route 51, Jefferson Hills, PA 15025 USA.

Patterned metal on silicon or glass wafers can be obtained from Sil'tronix (382 rue Louis Rustin, Technopole d'Archamps, 74160 Archamps, France) or University Wafer (11 Elkins Street, Unit 330, South Boston, MA 02127). Patterned metal on polymer substrates, including polyimide, polycarbonate, polyethylene naphthalate and polyethylene terephthalate may be obtained from VAST Films LTD (13525 Youngstown-Pittsburgh Rd, Petersburg, OH 44454). Peptides may be obtained from Genscript Corporation (860 Centennial Ave. Piscataway, NJ 08854, USA). Antibodies and antibody fragments may be obtained from Virusys Corporation (6370 Keysville Road, Keymar, MD 21757. Single-domain antibodies may be obtained from NanoTag Biotechnologies (Rudolf-Wissell-Straße 28a, 37079 Göttingen, Germany). Nanoparticles functioning as nanozymes can be obtained millipore sigma (400 Summit Drive Burlington, MA 01803). Lipids and kits for making liposomes are also available from millipore sigma.

Suitable continuous wave lasers for conducting Applicants can be obtained from Thorlabs (56 Sparta Avenue, Newtown, NJ 07860 USA), Coherent (5100 Patrick Henry Dr., Santa Clara, CA 95054 USA), and TLM Laser Ltd (Navigation Court, 1-arris Business Park, Stoke Prior, Bromsgrove, Worcestershire, B60 4FD UK). Pulsed lasers suitable for the applications described here include the Keyence MDX series of laser models obtained from Keyence Corporation (720 South Colorado Boulevard, Suite 650-S Denver, Colorado 80246A) which is capable of a selected range of pulse lengths between microseconds to milliseconds. Lasers with femtosecond and picosecond pulse widths suitable for the applications described here are available from Control Micro Systems (CMS) Laser (4420-A Metric Drive Winter Park, FL 32792). Lamps with characteristics suitable for the applications described here include the Pulse Forge 3300 model by manufactured by Novacentrix (400 Parker Dr. Suite 1110, Austin, TX).

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1: Laser Written resistor and capacitor in thin film molybdenum disulfide. A molybdenum disulfide (MoS$_2$) thin film of thickness totaling 900±50 nm was deposited onto a metal patterned glass or SiO$_2$ wafer via magnetron sputtering using a 99.95% pure MoS$_2$ target and Ti/Au contacts. The direct laser writing of resistors and capacitors was possible using a 514 nm laser and creating conducting MoO$_2$ patterns and insulating MoO$_3$ isolation with the Ti/Au contacts. The resistance can be controlled in a resistor component by varying the length of conductive material within the amorphous material, with the required MoO$_3$ isolation surrounding. Additionally, comb capacitors shown with tailored electronic properties are possible via patterning of the same materials but in different configurations.

Example 2: Gas sensor laser written in molybdenum disulfide Active circuit elements were also possible using the laser writing technique by taking advantage of the on/off properties of semiconducting 2H—MoS$_2$. One example of this is the laser writing of a chemresistor style gas sensor that can detect ammonia at sub 10 ppm levels. This chemresistor was composed of a semiconducting crystalline MoS$_2$ channel, metallic contact pads and electrodes, and a MoO$_3$ boundary isolation and was demonstrated to detect 10, 100, and 1000 parts per million of NH$_3$ gas.

Example 3: The first five materials listed in Column 4 of Table 1 below were made in accordance with Applicants' process on metallic contacts using a laser and then the same results were obtained using a lamp. Such materials are useful as listed in Column 5 of Table 1. The last 6 materials listed in Column 3 of Table 1 below are made in accordance with Applicants' process using a laser and then the same results were obtained using a lamp. Such materials are useful as listed in Column 5 of Table 1. The Examples in Table 1 row 1, 2, 5, 9 and 10 of column 4 show a crystalline structure changes in the starting material as represented by 2H, 1T, T-Phase and H-Phase while Examples in Table 1 row 3, 4, 6, 7, 8 and 9 of column 4 show a chemical change in the starting material.

TABLE 1

| Starting Material | Fluid blanket | Methodology | Post-annealed material | Use |
|---|---|---|---|---|
| Amorphous MoS$_2$ | Vacuum | Crystallization | 2H-MOS$_2$ | Semiconductor |
| | Vacuum | Crystallization | 1T-MOS$_2$ | Conductor |
| | Oxygen gas | Oxidation (Shorter annealing time) | MoO$_2$ | Conductor |
| | Oxygen gas | Oxidation (longer annealing time) | MoO$_3$ | Insulator |
| Amorphous WS$_2$ | Vacuum | Crystallization | 2H-WS$_2$ | Semiconductor |
| Amorphous TiS | Oxygen gas | Oxidation | TiO | Conductor |
| | Oxygen gas | Oxidation | TiO$_2$ | Semiconductor |
| | Nitrogen gas | Nitridization | TiN | Conductor |
| Amorphous VS$_2$ | Vacuum | Crystallization | T-phase VS$_2$ | Insulator |
| | Vacuum | Crystallization | H-phase VS$_2$ | Semiconductor |
| | Oxygen gas | Oxidation | VO$_2$ | Insulator |

Example 4. P-N junction with laser written MoS$_2$/WSe$_2$ Lateral P-N junctions are made possible through first deposition of metallic contacts followed by patterned amorphous deposition of in-plane heterjunctions of amorphous MoS$_2$/WSe$_2$ structures. With the use of one laser pass across the interface, a n-type semiconductor MoS$_2$ is in contact with a p-type WSe$_2$ semiconductor material, forming a P-N junction of use for light emitting diodes (LEDs) and other optical/electronic components.

Example 5: Sensor device with laser written MoS$_2$, patterned metal contacts and patterned ablated material. Multiplexed sensor devices require electrical isolation to ensure minimal cross-talk between laser written devices. With this in mind, laser patterned areas of crystallized MoS$_2$ were fabricated and the same laser was used to trace around the area that was annealed to remove all material within that region in creating an electrically isolated circuit. The ablation process removed in total about 1% area of the total $MoS_2$ film.

Figure 2:
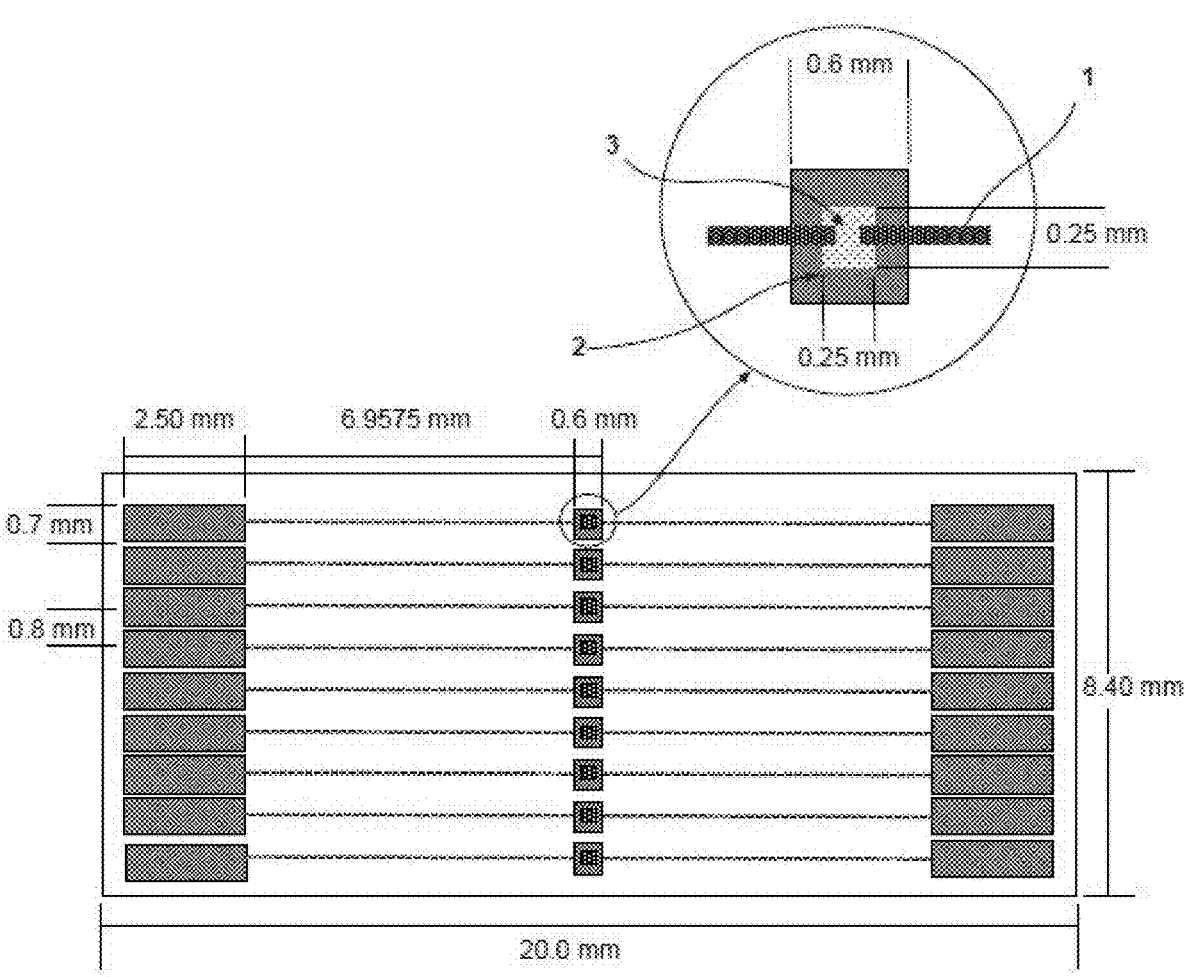
FIG. 2 is an example laser processed device configuration with deposited $MoS_2$ on prepatterned metal contacts and subsequent conversion showing in additional detail Metal electrodes (1), Amorphous $MoS_2$ (2) and Laser crystallized $MoS_2$ (3)
Figure 3A:
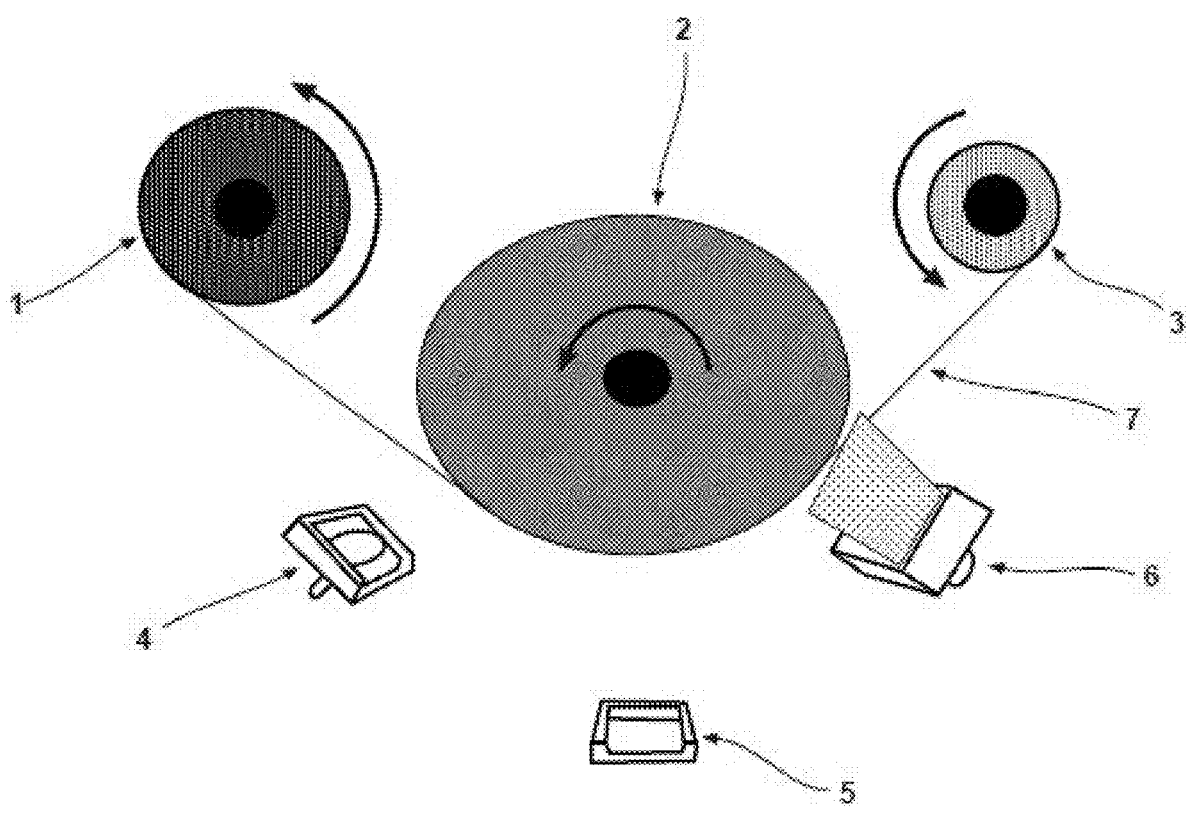
FIG. 3A is an example of the first unit operation in a roll-to-roll deposition of $MoS_2$ onto metal patterned substrates with subsequent laser annealing showing Feed roll (1), Main roller (2), Receiving roller (3), $MoS_2$ sputtering target (4), Laser (5), Metal sputtering target (6) and Flexible glass substrate (7).
Figure 3B:
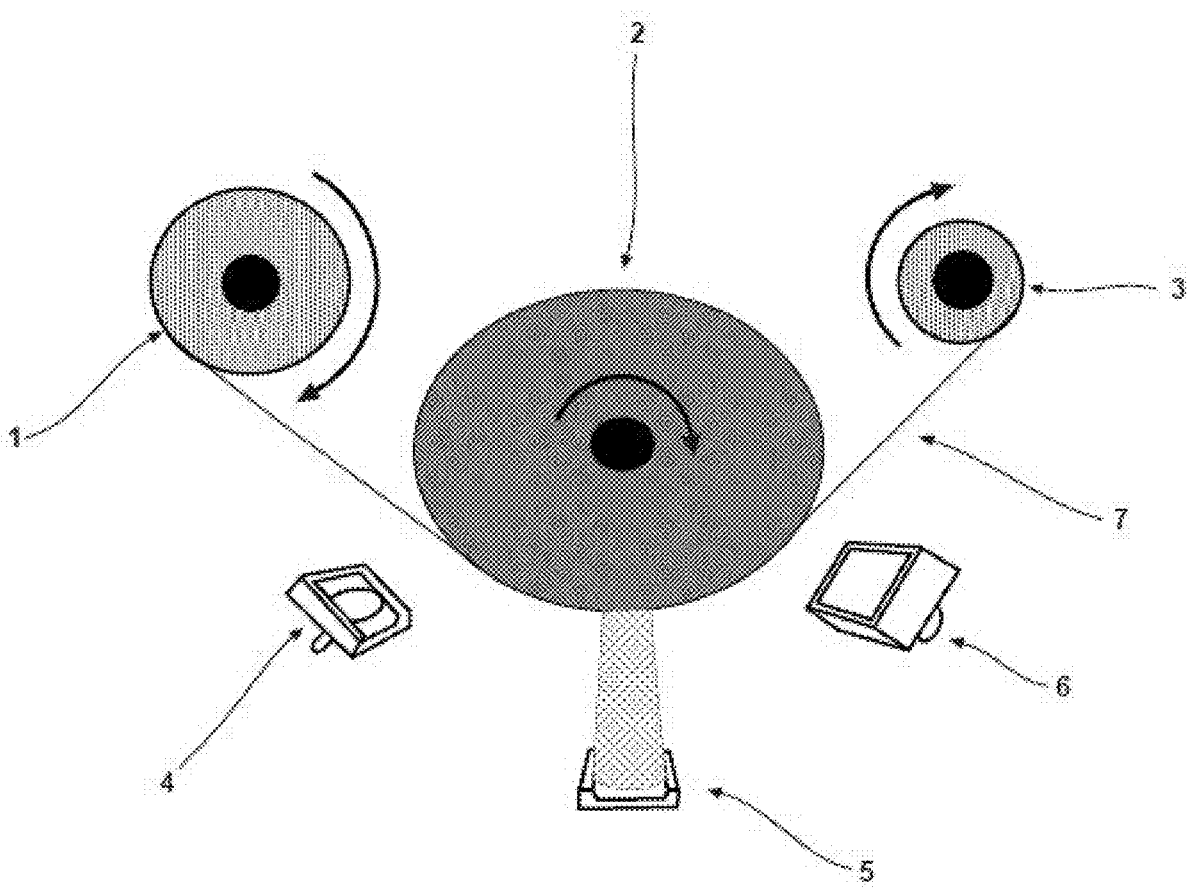
FIG. 3B is an example of a second unit operation in a roll-to-roll deposition of $MoS_2$ onto metal patterned substrates with subsequent laser annealing showing Receiving roll (1), Main roller (2), Feed roll (3), $MoS_2$ sputtering target (4), Laser (5), Metal sputtering target (6), and Flexible glass substrate (7).
Figure 3C:
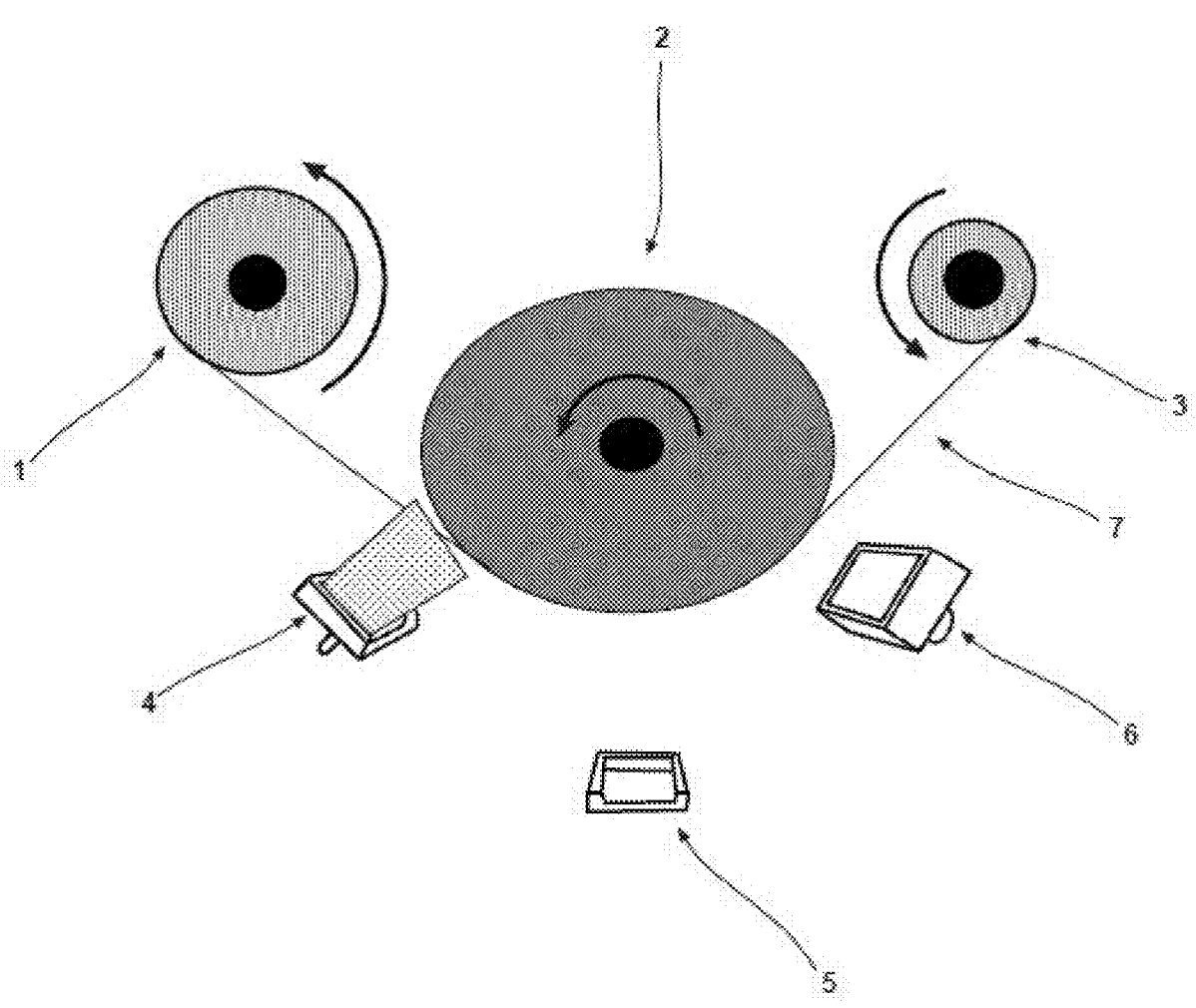
FIG. 3C is an example of a third unit operation in a roll-to-roll deposition of $MoS_2$ onto metal patterned substrates with subsequent laser annealing showing Feed roll (1), Main roller (2), Receiving roller (3), $MoS_2$ sputtering target (4), Laser (5), Metal sputtering target (6), and Flexible glass substrate (7).
Figure 3D:
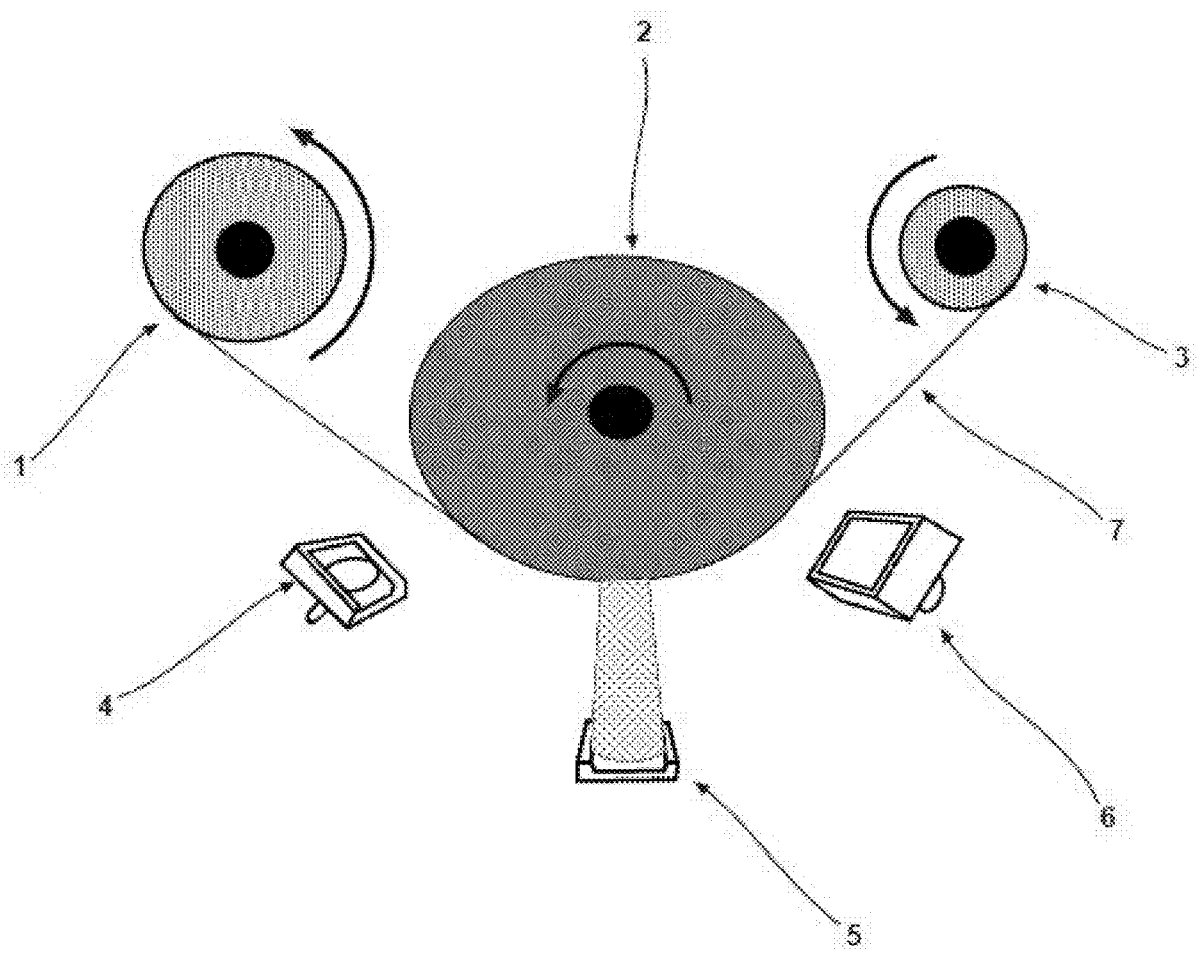
FIG. 3D is an example of a fourth unit operation in a roll-to-roll deposition of $MoS_2$ onto metal patterned substrates with subsequent laser annealing showing Receiving roll (1), Main roller (2), Feed roll (3), $MoS_2$ sputtering target (4), Laser (5), Metal sputtering target (6), and Flexible glass substrate (7).
Figure 4:
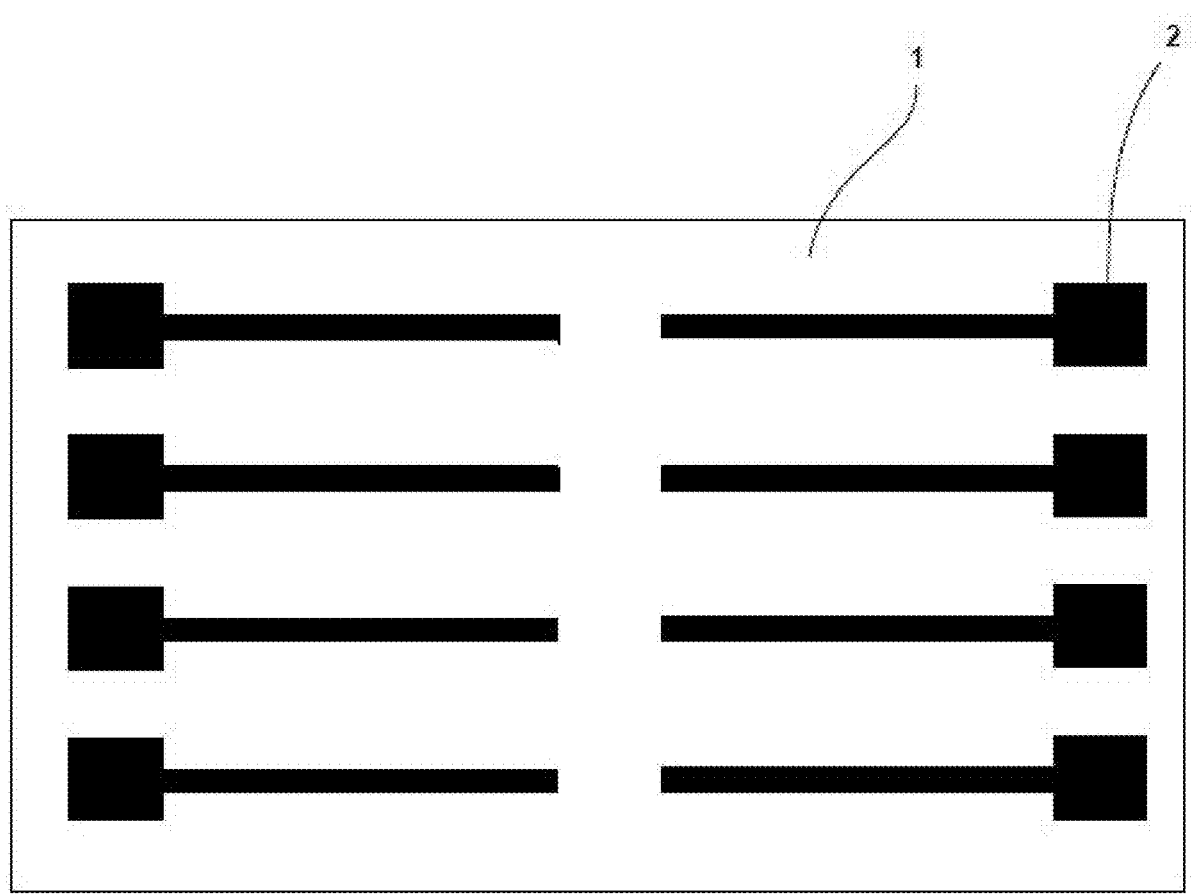
FIG. 4 is an example of a pattern for the pattern illumination-based annealed, coated substrate's patterned electrical conductive material (2) on a substrate (1) of the present invention.
Figure 5:
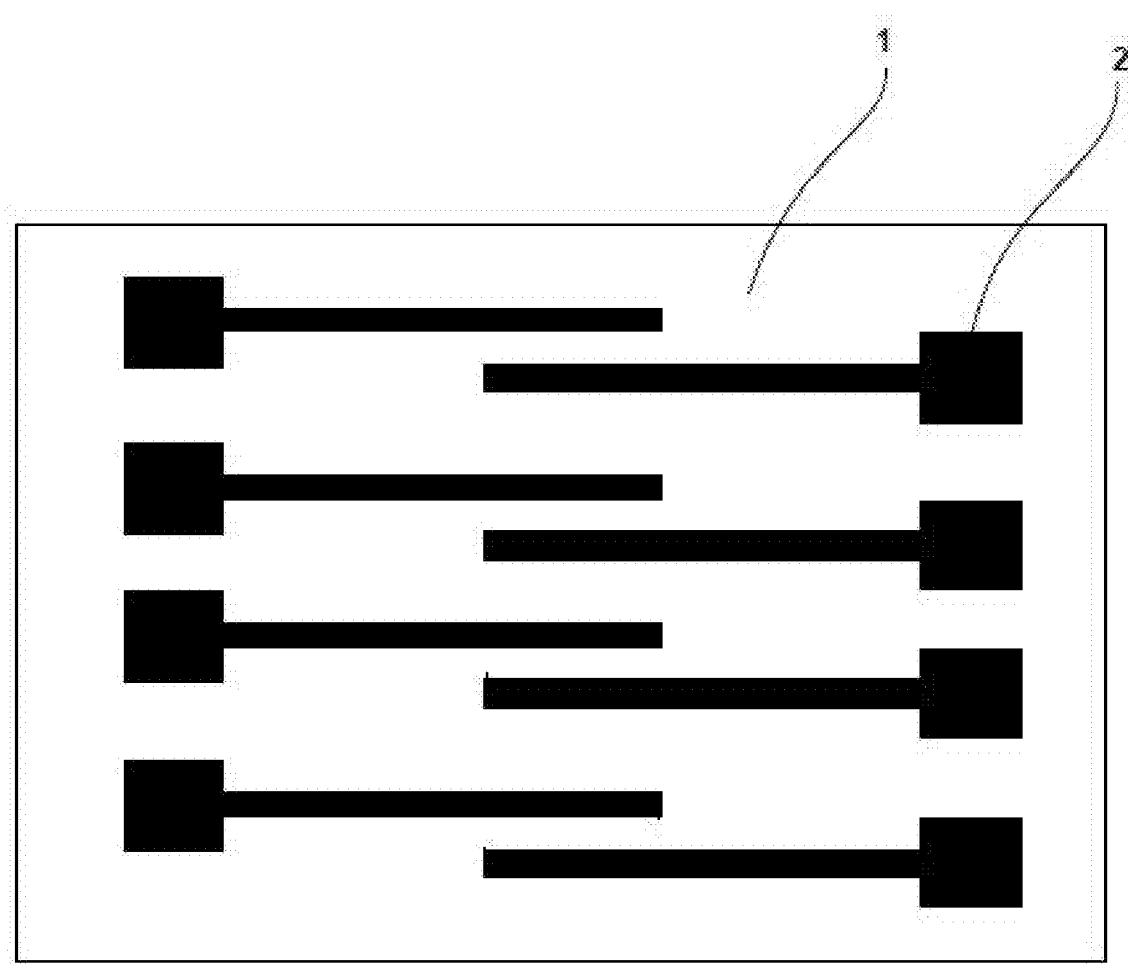
FIG. 5 is an example of a pattern for the pattern illumination-based annealed, coated substrate's patterned electrical conductive material (2) on a substrate (1) of the present invention.
Figure 6:
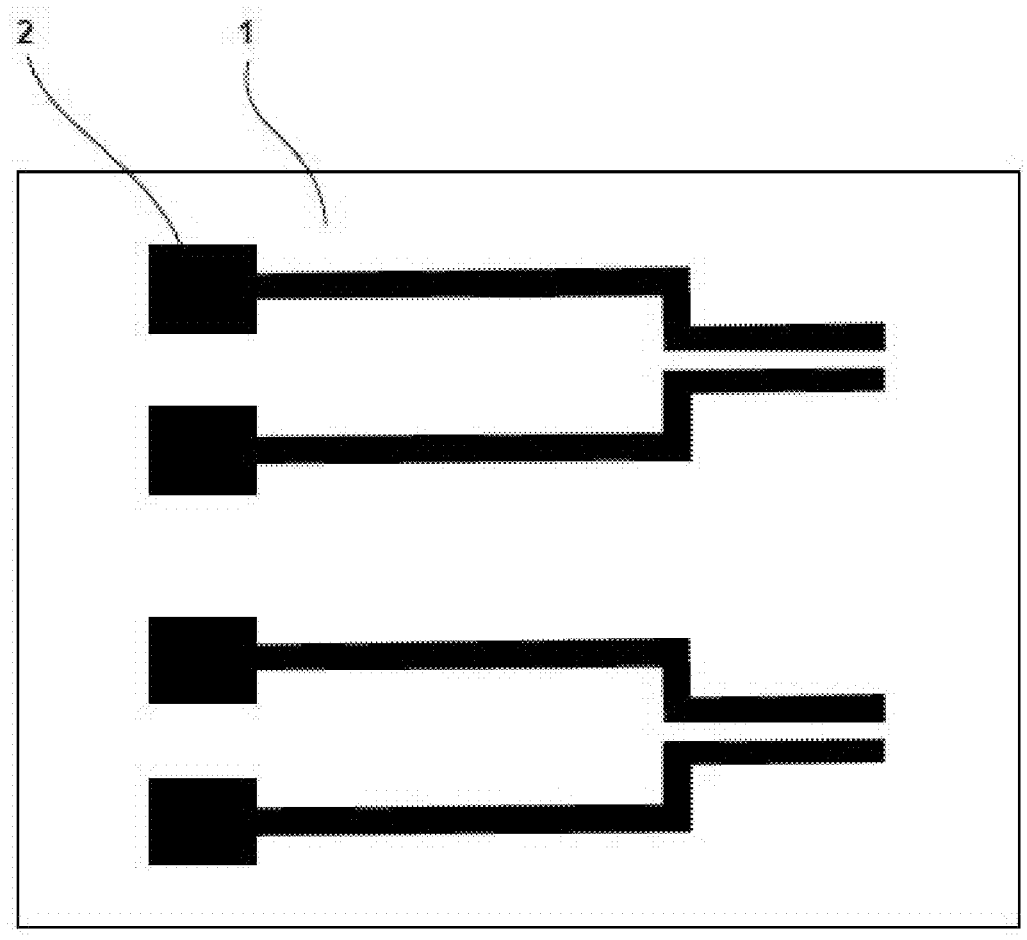
FIG. 6 is an example of a pattern for the pattern illumination-based annealed, coated substrate's patterned electrical conductive material (2) on a substrate (1) of the present invention.
Figure 7:
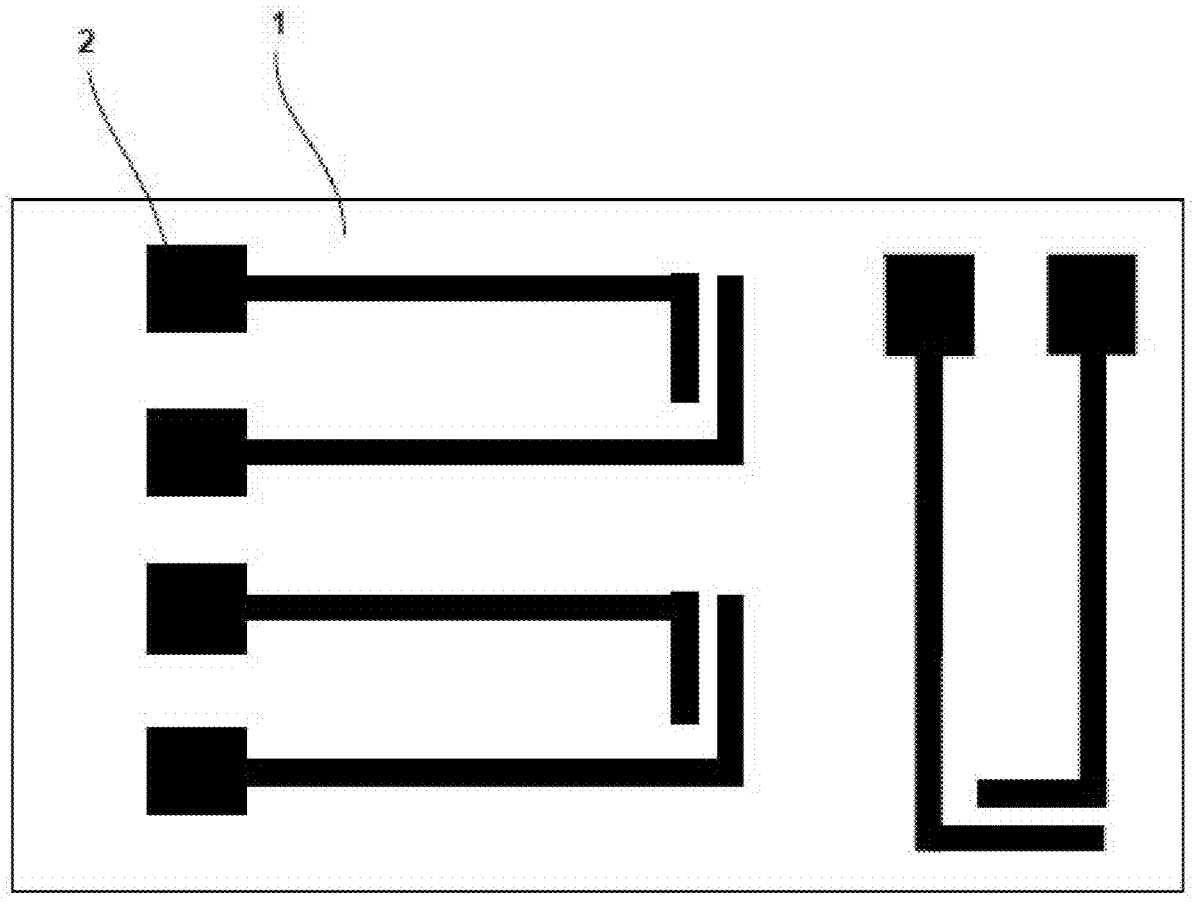
FIG. 7 is an example of a pattern for the pattern illumination-based annealed, coated substrate's patterned electrical conductive material (2) on a substrate (1) of the present invention.
Figure 8:
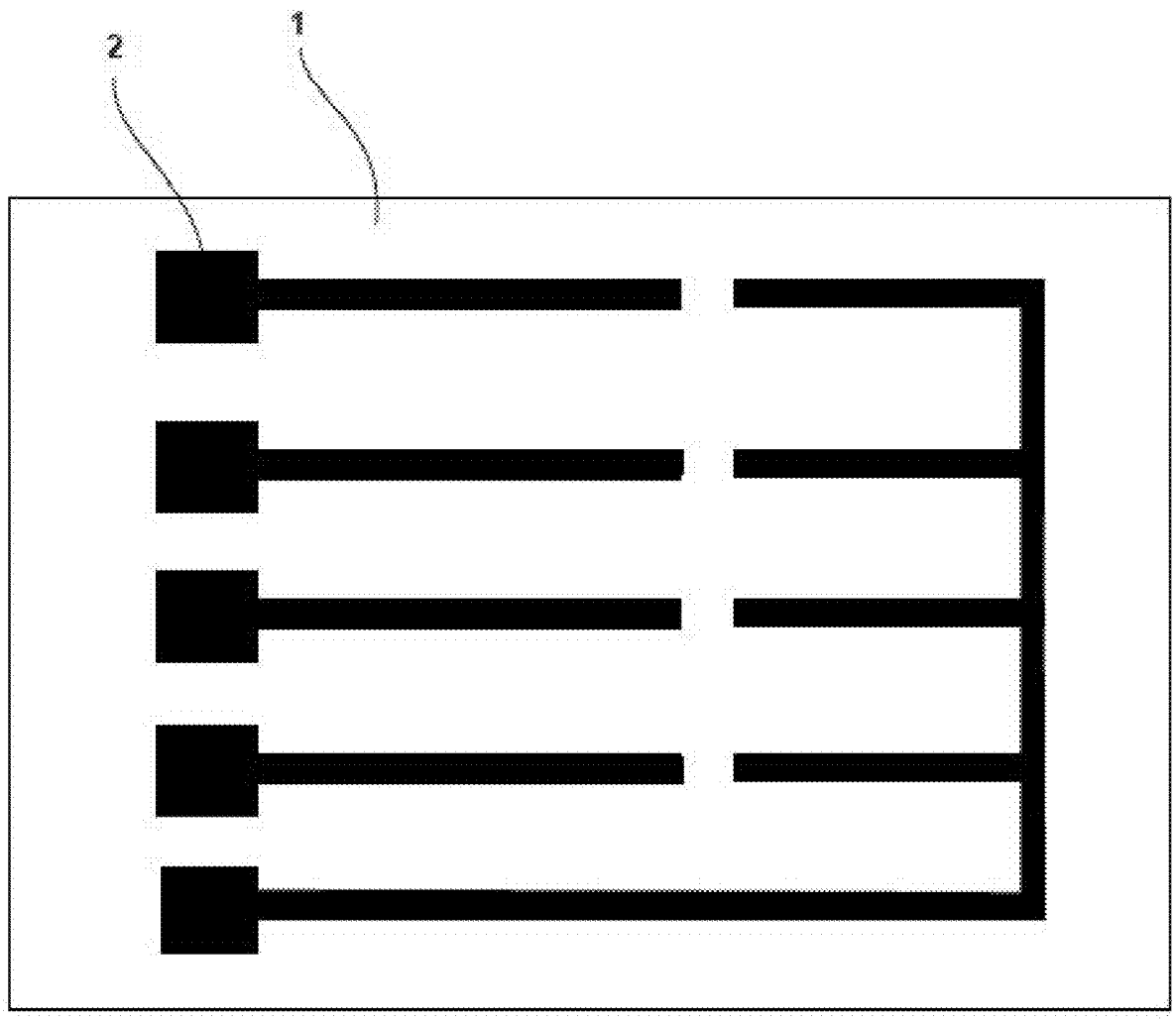
FIG. 8 is an example of a pattern for the pattern illumination-based annealed, coated substrate's patterned electrical conductive material (2) on a substrate (1) of the present invention.
Figure 9:
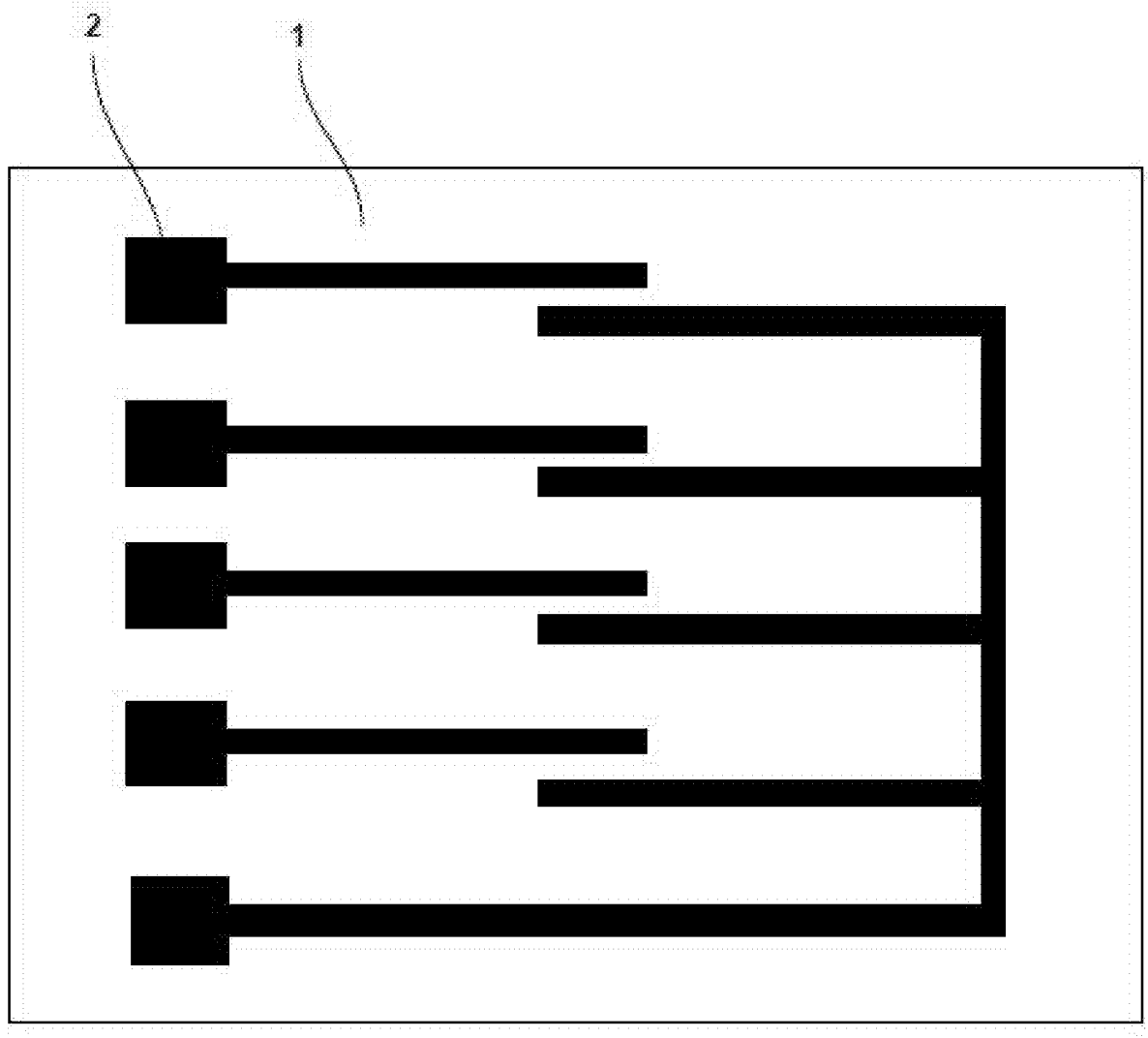
FIG. 9 is an example of a pattern for the pattern illumination-based annealed, coated substrate's patterned electrical conductive material (2) on a substrate (1) of the present invention.

Example 6: Laser written chemical or biological sensor on e-beam evaporated patterned metal on glass substrate. A prepatterned metal film composed of gold or molybdenum metal in a pattern was first deposited on a glass substrate as depicted in FIG. 1 and FIG. 2. A thin 3 nm molybdenum disulfide film is then sputter coated onto the glass/patterned metal substrate to form a continuous thin film. A CW laser is then utilized to crystallize the amorphous $MoS_2$ film to convert into semiconducting $2H$—$MoS_2$ for sensing applications. The chemical sensor is then electrically isolated through laser ablation removal of the amorphous $MoS_2$ film around the crystallized $2H$—$MoS_2$ to form a chem/bio sensor configuration.

Example 7: All laser written sensor on ablated metal pattern in roll-to-roll configuration. A roll-to-roll process is utilized to run a spool of flexible glass through a sputter-coater, laser processing system as depicted in FIG. 3. First, a thin layer of molybdenum or gold metal is deposited over the entire glass substrate and the laser is used to ablate a pattern in such a configuration as identified in FIGS. 4-9. The laser-ablated patterned metal film is then coated with 3 nm $MoS_2$ over the entire glass/metal substrate. Immediately following, a laser ablation step is used to remove all or some fraction of the amorphous $MoS_2$ except an area connecting the metal contacts, which is then laser annealed at a lower laser energy condition than that used for ablation to induce crystallization in a phase such as the hexagonal $2H$—$MoS_2$ formation. The resultant devices are an embodiment of an all-laser fabrication roll-to-roll approach for chem/bio sensor fabrication.

Figure 10:
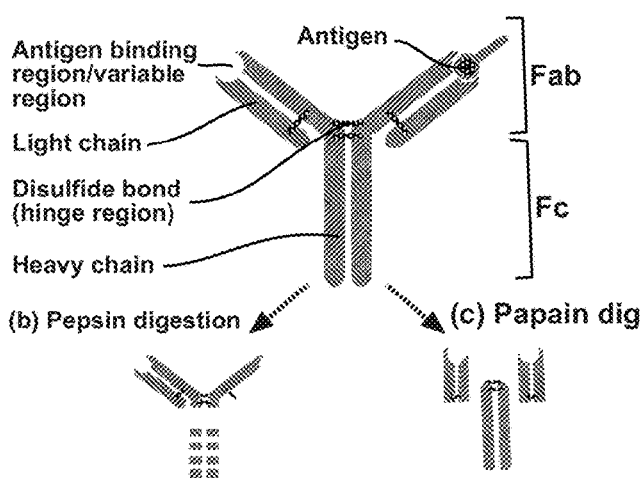
FIG. 10 is an example of biomolecular interactions with sensor devices to promote specific interactions with a target biomolecule.
Figure 10:
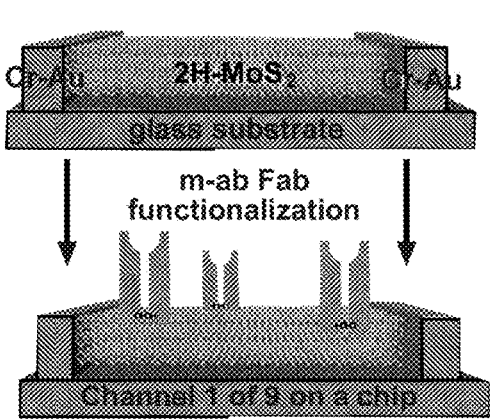

Example 8: For direct binding of proteins, the sulfur chemistry of antibody fragments at their cysteine and proline-rich hinge region may be exposed via papain digestion to interact with the $MoS_2$ region of the sensor device which may have some concentration of atomic sulfur vacancies as shown in FIG. 10. The presence of these vacancies may result in interactions that may include covalent or electrostatic binding of antibody fragments or some combination thereof.

Figure 11A:
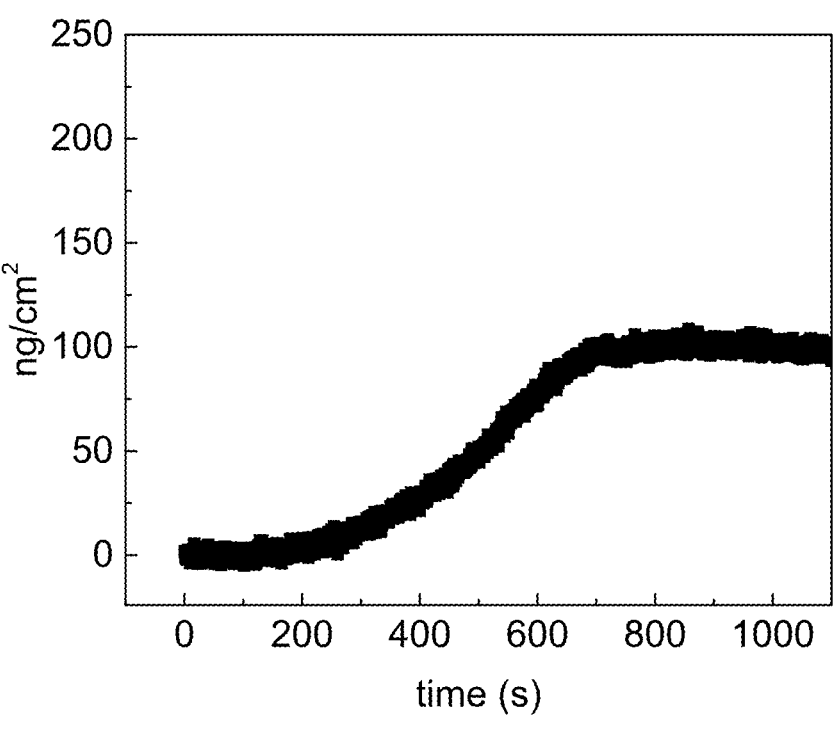
FIG. 11A is an example of measurement of mass accumulation rate (concentration of 2,000 ng/mL over time) of a peptide having SEQ. ID 2 terminated with two leucine amino acids to strengthen interactions with the $MoS_2$ substrate.
Figure 11B:
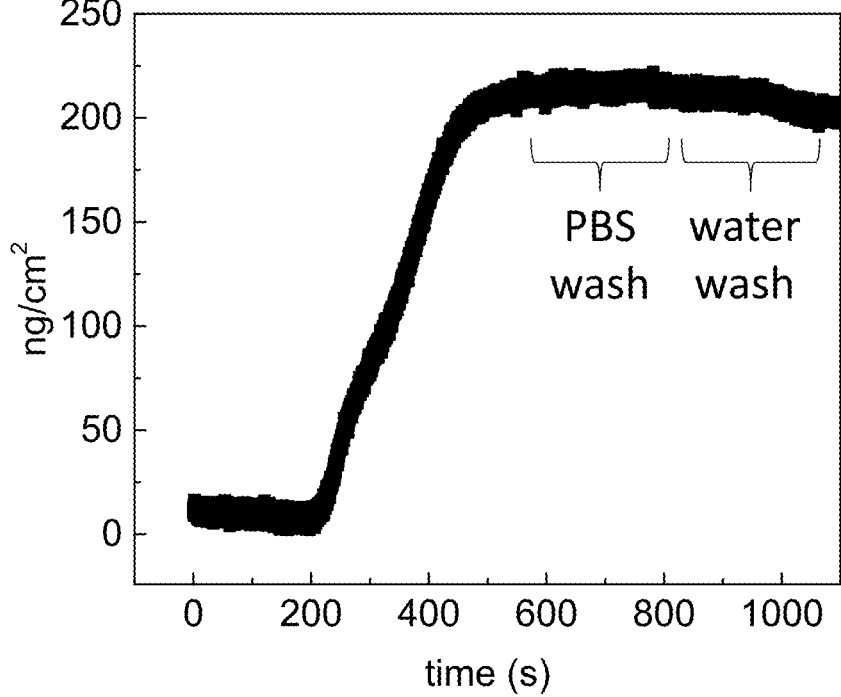
FIG. 11B shows attachment of a concentration of 10,000 ng/mL of the peptide having SEQ. ID 2 over time, with washing steps in phosphate buffered saline and water after attachment with little or no mass loss during washing steps.

Example 9: Addition of amino acids to a target-binding peptide for interaction of target binding peptide with sensor surface is shown in FIG. 11. Two leucine amino acids are added to a c-TnI binding peptide. Interaction strength of the peptide with the sensor surface may be due in part to formation of a hydrophobic pocket with the leucine addition. Accumulation rates are shown for flowing solutions of two different peptide concentrations in a 1× concentration of phosphate buffered saline (PBS) on a $MoS_2$ surface. For the higher peptide concentration example, washing of the surface with 1× concentration phosphate buffer solution or doubly deionized water does not change the accumulated mass, suggesting strong interactions between the modified peptide and the $MoS_2$ substrate.

Figure 12A:
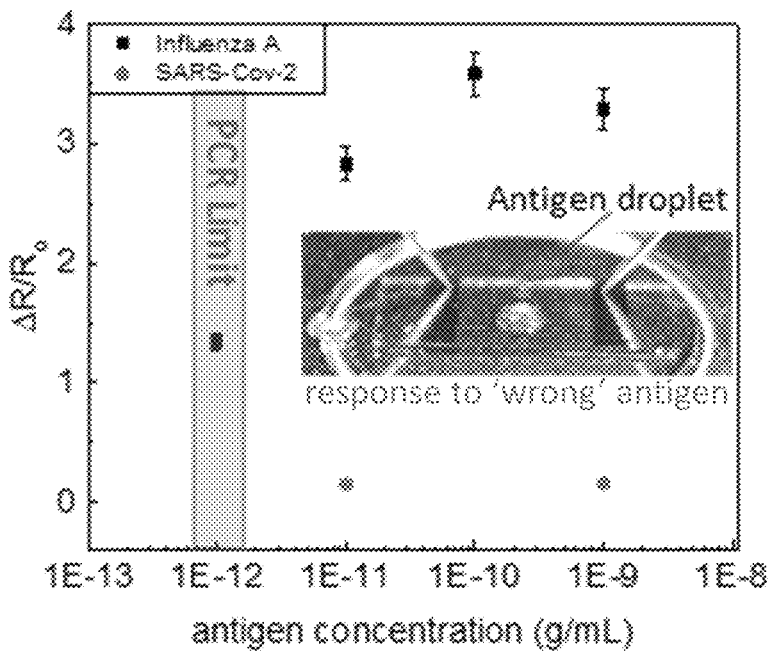
FIG. 12A is an example of electrical measurements from a sensor device with a laser-illuminated $MoS_2$-based rectangular sensor area (approximately 250 micrometers by 200 micrometers) with a concentration of influenza A hemagglutinin (HA) monoclonal antibody fragments applied to the surface via pipetting of a solution containing the antibody fragments in a buffer solution. Measurements of relative resistance changes for the indicated concentrations of Influenza A hemagglutinin and also the indicated concentrations of SARS-CoV-2 spike protein are depicted.
Figure 12B:
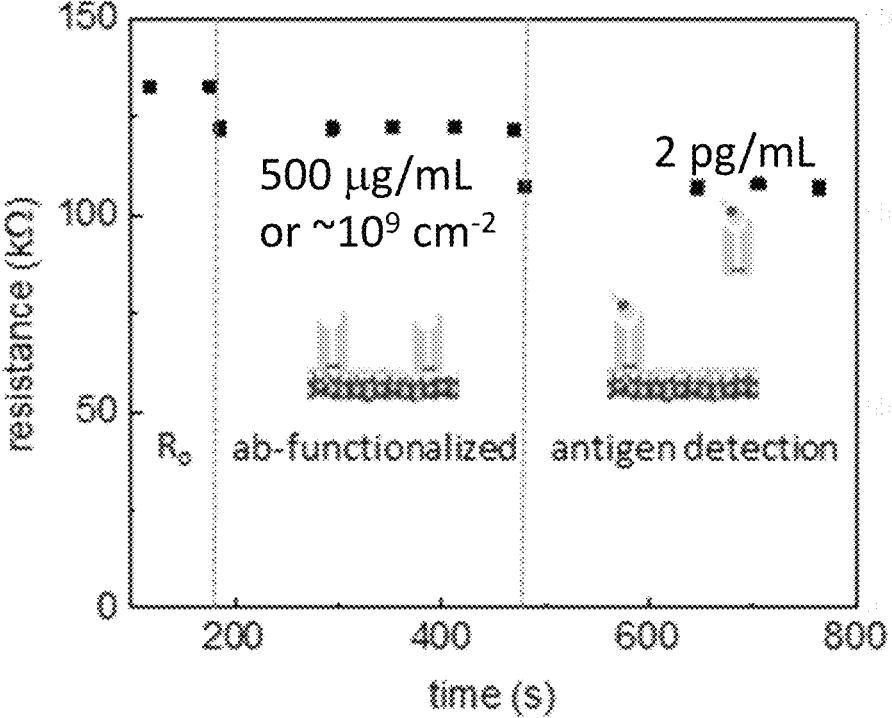
FIG. 12B shows the time response of resistance for a sensor device during functionalization with influenza A hemagglutinin (HA) monoclonal antibody fragments and subsequent attachment of influenza A hemagglutinin at the times indicated on the figure.

Example 10: A single chip with multiple sensors and antibody fragments applied for specific binding to a target analyte of interest is shown in FIG. 12. On two sensor devices functionalized with influenza A HA protein monoclonal antibody fragments, concentrations of SARS-CoV2 spike protein (as indicated by the x axis) were applied and a much smaller sensor response was observed that at the same concentration of the complementary influenza HA analyte, demonstrating the utility of antibody functionalization for specific detection. The time response of the sensor is shown where a change in resistance is recorded within seconds of the application of the antibody fragments suggesting a rapid interaction once applied. The response time for application of the analyte is also shown to be within seconds which is expected for sensors with dimensions on the order of ~100 micrometers.

Example 11: Thick $MoS_2$ with laser annealing and metal contacts occurring on or within the film to form 3D device. A thick (100 micrometers) amorphous film of $MoS_2$ is deposited onto a glass substrate with patterned metal contacts. A sensor device is laser annealed into the film occur in several stepwise procedures both at the surface of the film and within the depth. First, an area of the film outside of the active device area is laser ablated where the entirety of the film is removed in select areas. Within the remaining film, a focused nanosecond laser is used to crystallize the surface of $MoS_2$ (<1 micrometer) for the active region of the sensor, leaving the remaining 99% within the thickness unaltered. Then, a continuous wave laser is used to oxidize regions of the film through the entire thickness in order to form conductive $MoO_3$ to serve as isolation in a multiplex sensor device. Finally, a peptide molecule is attached to the laser treated crystallized $MoS_2$ region in order to operate as a biomolecular sensor selective to the antigen of interest.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and process, and illustrative examples shown and described. Accordingly, departures may be made from such details without departing from the scope of the general inventive concept.

What is claimed is:

1. A process of making a sensor, said process comprising;

a) applying one or more coatings of electrically conductive material to a substrate, which substrate has a first side and a second side, said one or more coatings of electrically conductive material being applied to at least the first side of said substrate;

b) removing a portion of said electrically conductive material to form a pattern of electrically conductive material electrodes on said substrate;

c) applying one or more chemical coatings in the form of a continuous film over said patterned electrical conductive material to form a coated substrate, wherein said patterned electrical conductive material comprises a material selected from the group consisting of: poly(3,4-ethylenedioxythiophene), poly(3,4-ethylenedioxythiophene) polystyrene sulfonate, poly(pyrrole), polycarbazoles, polyindoles, polyazepines, Cr, Mo, Ti, Sc, Ni, V, Hf, W, Nb, Au, Ag, Cu, and Pt, and mixtures thereof, and said one or more chemical coatings disposed over said one or more coatings of patterned electrical conductive material each independently comprise a transition metal and an element selected from the group consisting of: hydrogen, carbon, nitrogen, oxygen, sulfur, selenium, phosphorous, and mixtures thereof, wherein said one or more chemical coatings each independently comprising at least one of an amorphous, nanocrystalline, microcrystalline or crystalline region;

d) pattern illumination-based annealing said coated substrate, said pattern illumination-based annealing comprising using one or more lasers and/or lamps to achieve at least one of a chemical change or a change in crystallization in at least a portion of at least one of said one or more chemical coatings on at least one side of said substrate; and e) attaching one or more types of functional molecules and/or one or more complexes comprising one or more types of functional molecules and one or more target molecules to at least a portion of said pattern illumination-based anneal coated substrate, said one or types of functional molecules being attached by:

(i) attaching said one or more functional molecules and/or one or more complexes to an annealed portion on the surface of said pattern illumination-based anneal coated substrate at vacancies in the surface of the chemical coating that create bonding sites for said functional molecules; and/or (ii) bonding a peptide to said pattern illumination-based anneal coated substrate and attaching said one or more functional molecules to said peptide.

2. A process of making a sensor according to claim 1 wherein said one or more functional molecules are biomaterials that are selected from the group consisting of: peptides, nanozymes, proteins, lipids, carbohydrates and lectins, nucleic acids, and mixtures thereof.

3. A process of making a sensor according to claim 2 wherein said biomaterial's attachment to said pattern illumination-based anneal coated substrate comprises at least one of a covalent bond, electrostatic bond, or a covalent and electrostatic bond.

4. A process of making a sensor according to claim 2 wherein said attaching said biomaterials to said pattern illumination-based anneal coated substrate comprises contacting said at least a portion of said pattern illumination-based anneal coated substrate and said one or more types of biomaterials.

5. A process of making a sensor according to claim 1 wherein:

at least one of said one or more chemical coatings comprises, prior to said annealing, two or more regions that are amorphous, nanocrystalline, microcrystalline or crystalline with the proviso that at least two of said regions are not identical with respect to being amorphous, nanocrystalline, microcrystalline or crystalline and said laser or lamp forms on, within or on and within said at least one of said one or more chemical coatings:

(i) at least two electronic elements selected from a conductor, semiconductor and an insulator;

(ii) two or more different conductors having at least one of the following: different electrical properties or different optical properties;

(iii) two or more different semiconductors having at least one of the following: different electrical properties or different optical properties; or (iv) two or more different insulators having at least one of the following:
different electrical properties or different optical properties;

said process being performed under one of the following conditions: vacuum of less 100 torr, air or under a fluid blanket other than air; and said pattern illumination-based annealing results in at least one of a chemical change or a change in crystallization, or the removal of at least a portion of at least one of said one or more chemical coatings and resulting in an electrical component, an optical component or a combined electrical and optical component being formed on, within or on and within at least a portion of said pattern illumination-based annealed one or more chemical coatings.

6. The process of claim 1 further comprising performing steps a) to e) on the second side of said substrate as well.

7. The process of claim 1 wherein said transition metal is selected from the group consisting of molybdenum, tungsten, niobium, tantalum, vanadium, titanium, chromium, iron, rhodium, hafnium, rhenium and mixtures thereof.

8. A process according to claim 1 wherein said one or types of functional molecules are primarily attached to said pattern illumination-based anneal coated substrate by bonding a peptide to said pattern illumination-based anneal coated substrate and attaching said one or more functional molecules to said peptide.

9. The process of claim 5 wherein, said electrical and/or optical component is selected from the group consisting of an inductor, a capacitor, a resistor, a diode, a a trace, a battery, an optical filter, a chemical sensor, a biological sensor and a solar cell.

10. The process of claim 1 wherein said pattern illumination-based annealing in step d) further comprises removal of at least a portion of said chemical coating on at least one side of said substrate, and each of said one or more chemical coatings have an area and a thickness and said removal of said at least a portion of said one or more chemical coating occurs, said removal comprising at least one of:

a.) laser ablation removal of from about 0.1% to about 99.9% of at least one of said one or more chemical coatings' area; or b.) laser ablation removal of at least 85% of at least one of said chemical coatings' thickness; or laser ablation removal of about 85% to about 99% of at least one of said chemical coatings' thickness.

11. The process of claim 1, said process being a roll process wherein said coated chemically substrate is a rolled coated chemically substrate that is unrolled at least in part, said unrolled chemical coating portion of said coated substrate being at least in part pattern illumination-based annealed.

12. The process of claim 1 wherein said substrate of said coated substrate is selected from glass, polymer and mixtures thereof.

13. The process of claim 1 wherein at least a portion of said coated substrate's pattern illumination-based annealed chemical coating is further treated by at least one of the following processes:

a.) two or more pattern illumination-based annealings;

b.) plasma treatment comprising exposing said at least a portion of said coated substrate's pattern illumination-based annealed chemical coating to an ionized gas derived from the group consisting of He, Ne, Ar, Kr, Xe, $H_2$, $O_2$, $SF_6$, $CF_4$, $N_2$ and mixtures thereof;

c.) ion beam irradiation comprising exposing said at least a portion of said coated substrate's pattern illumination-based annealed chemical coating to an ion beam, said ion beam comprising an ionized gas derived from the group consisting of He, Ne, Ar, Kr, Xe, $H_2$, $O_2$, $SF_6$, $CF_4$, $N_2$ and mixtures thereof;

d.) electron beam illumination comprising at least a portion of said coated substrate's pattern illumination-based annealed chemical coating to an electron dose of from about $10^2$ electrons/$nm^2$ to about $10^{25}$ electrons/$nm^2$;

e.) thermal annealing said at least a portion of said coated substrate's pattern illumination-based annealed chemical coating, said at least a portion of said coated substrate's pattern illumination-based annealed chemical coating's thermal annealing treatment temperature being from about 250° C. to about 1,500° C.;

f.) chemically etching said at least a portion of said coated substrate's pattern illumination-based annealed chemical coating comprising contacting said at least a portion of said coated substrate's pattern illumination-based annealed chemical coating with an etching composition;

g.) electro-chemically treating said at least a portion of said coated substrate's pattern illumination-based annealed chemical coating by contacting said at least a portion of said coated substrate's pattern illumination-based annealed chemical coating with a chemical composition comprising an electrolyte and subjecting said contacted at least a portion of said coated substrate's pattern illumination-based annealed chemical coating and said chemical composition comprising an electrolyte to an electrical current;

h.) surface physical modification of at least a portion of said coated substrate's pattern illumination-based annealed chemical coating.

14. The process of claim 1 wherein each target is independently a chemical target or a biological target.

15. The process of claim 1 wherein said step c) of applying one or more chemical coatings in the form of a continuous film over said patterned electrical conductive material to form a coated substrate comprises applying said one or more chemical coatings using a chemical or physical vapor deposition process.

16. The process of claim 1 wherein said pattern illumination-based annealing results in a change in the molecular composition in a region of at least one of said materials that results in an electrical component, an optical component or a combined electrical and optical component being formed on, within or on and within said material.

17. The process of claim 16 wherein the transition metal is Mo, and the element is oxygen, and the process forms different oxide phases $MoO_2$ and $MoO_3$ on, within, or on and within said material.

18. The process of claim 7 wherein said transition metal is selected from the group consisting of: niobium, tantalum, vanadium, titanium, chromium, iron, rhodium, hafnium, rhenium, and mixtures thereof.

19. The process of claim 1 wherein at least a portion of said coated substrate's pattern illumination-based annealed chemical coating is further treated by at least one of the following processes:

a) plasma treatment comprising exposing said at least a portion of said coated substrate's pattern illumination-based annealed chemical coating to an ionized gas derived from the group consisting of He, Ne, Ar, Kr, Xe, $H_2$, $O_2$, $SF_6$, $CF_4$, $N_2$ and mixtures thereof;

b) ion beam irradiation comprising exposing said at least a portion of said coated substrate's pattern illumination-based annealed chemical coating to an ion beam, said ion beam comprising an ionized gas derived from the group consisting of He, Ne, Ar, Kr, Xe, $H_2$, $O_2$, $SF_6$, $CF_4$, $N_2$ and mixtures thereof;

c) electron beam illumination comprising at least a portion of said coated substrate's pattern illumination-based annealed chemical coating to an electron dose of from about $10^2$ electrons/$nm^2$ to about $10^{25}$ electrons/$nm^2$ d) chemically etching said at least a portion of said coated substrate's pattern illumination-based annealed chemical coating comprising contacting said at least a portion of said coated substrate's pattern illumination-based annealed chemical coating with an etching composition;

e) electro-chemically treating said at least a portion of said coated substrate's pattern illumination-based annealed chemical coating by contacting said at least a portion of said coated substrate's pattern illumination-based annealed chemical coating with a chemical composition comprising an electrolyte and subjecting said contacted at least a portion of said coated substrate's pattern illumination-based annealed chemical coating and said chemical composition comprising an electrolyte to an electrical current; and f) surface physical modification of at least a portion of said coated substrate's pattern illumination-based annealed chemical coating.

20. A process of making a sensor according to claim 1 wherein said one or more functional molecules are biomaterials that are selected from the group consisting of: peptides, nanozymes, lipids, carbohydrates and lectins, nucleic acids, and mixtures thereof.

21. A process of making a sensor according to claim 2 wherein said biomaterial's attachment to said pattern illumination-based anneal coated substrate comprises an electrostatic bond.

22. The process of claim 1 wherein said one or more types of functional molecules comprise a 12-mer peptide having SEQ. ID 1.

23. The process of claim 1 wherein said one or more types of functional molecules comprise a peptide having SEQ. ID 2 that is functionalized with two leucine amino acids for detecting cardiac troponin (cTnl).

24. The process of claim 1 wherein said one or more types of functional molecules comprise a peptide having SEQ. ID 3 to bind to alanine aminotransferase.

25. The process of claim 1 wherein said one or more types of functional molecules comprise at least one of the following:

1) the peptide having SEQ. ID 4 for detecting HIV1 protease;
2) the peptide having SEQ ID 5 for detecting trypsin;
3) the peptide having SEQ. ID 6 for detection of Caspase 3; or
4) the peptide having SEQ. ID 7 for detection of MMP-7.

26. The process of claim 1 wherein said one or more types of functional molecules comprise proteins selected from the group consisting of: antibodies, antibody fragments, antibody mimics, single domain antibodies, enzymes, and mixtures thereof, wherein the process comprises using at least one of the following:

1) antibodies and antibody fragments to bind to surface proteins on viruses, said viruses including SARS-Co V2 and Influenza A;
2) antibodies and antibody fragments to bind to bacteria, including *Streptococcus pyogenes;*
3) antibodies and antibody fragments to bind to human hormones;
4) antibodies and antibody fragments to bind to proteins native to the human body, including cardiac troponin;
5) antibodies and antibody fragments to bind to substances foreign to the human body, including THC (tetrahydrocannabinol) and narcotics;
6) the angiotensin-converting enzyme 2 (ACE2) to bind to spike proteins of the SARS-Co V and SARS-Co V2 viruses.

27. The process of claim 1 wherein said one or more target molecules comprise: proteins, lipids, and carbohydrates, target molecules include aromatics, aromatic halogens, halocarbon, polar aprotics, volatile organic compounds, hazardous gases, for example, arsenic, radon, nitrogen dioxide, carbon monoxide, carbon dioxide, carbon disulfide, ammonia, napthalene, isoprene, terpenes, methanol, benzyl chloride, hexachloro-1,3-butadiene, tribomomethane, and 1,4-dioxane.

\* \* \* \* \*

SEQUENCE LISTING

<160> NUMBER OF SEQ ID NOS: 7

<210> SEQ ID NO 1
<211> LENGTH: 12

```
<212> TYPE: PRT
<213> ORGANISM: Artificial Sequence
<220> FEATURE:
<223> OTHER INFORMATION: Artificial Sequence Obtained Through Biopanning

<400> SEQUENCE: 1

His Leu Leu Gln Pro Thr Gln Asn Pro Phe Arg Asn
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 2

Phe Tyr Ser His Ser Phe His Glu Asn Trp Pro Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Artificial Sequence Obtained Through Biopanning

<400> SEQUENCE: 3

Trp His Trp Arg Asn Pro Asp Phe Trp Tyr Leu Lys
1               5                   10

<210> SEQ ID NO 4
<211> LENGTH: 19
<212> TYPE: PRT
<213> ORGANISM: Artificial Sequence
<220> FEATURE:
<223> OTHER INFORMATION: Artificial Sequence Obtained Through Biopanning

<400> SEQUENCE: 4

Asp Ala Asx Cys Tyr Leu Ser Gln Asn Tyr Pro Ile Val Gln Glu Asp
1               5                   10                  15

Ala Asn Ser

<210> SEQ ID NO 5
<211> LENGTH: 21
<212> TYPE: PRT
<213> ORGANISM: Artificial Sequence
<220> FEATURE:
<223> OTHER INFORMATION: Artificial Sequence Obtained Through Biopanning
<220> FEATURE:
<221> NAME/KEY: misc_feature
<222> LOCATION: (10)..(10)
<223> OTHER INFORMATION: Xaa can be any naturally occurring amino acid

<400> SEQUENCE: 5

Asp Ala Asx Cys Tyr Leu Gly Pro Ala Xaa Ala Ala Leu Ala Ile Gly
1               5                   10                  15

Glu Asp Ala Asn Ser
            20

<210> SEQ ID NO 6
<211> LENGTH: 8
<212> TYPE: PRT
<213> ORGANISM: Artificial Sequence
<220> FEATURE:
<223> OTHER INFORMATION: Artificial Sequence Obtained Through Biopanning
```

-continued

```
<400> SEQUENCE: 6

Ser Gly Asp Glu Val Asp Ser Gly
1               5

<210> SEQ ID NO 7
<211> LENGTH: 9
<212> TYPE: PRT
<213> ORGANISM: Artificial Sequence
<220> FEATURE:
<223> OTHER INFORMATION: Artificial Sequence Obtained Through Biopanning

<400> SEQUENCE: 7

Arg Pro Leu Ala Leu Trp Arg Ser Cys
1               5
```